(12) United States Patent
Fletcher et al.

(10) Patent No.: US 8,747,379 B2
(45) Date of Patent: *Jun. 10, 2014

(54) ABSORBENT ARTICLES WITH REFASTENABLE SIDE SEAMS

(75) Inventors: Amy Lynn Fletcher, Appleton, WI (US); Lisa Ann Dimitrijevs, Appleton, WI (US); Christopher Peter Olson, Neenah, WI (US); Kathleen Irene Ratliff, Neenah, WI (US); Shirlee Ann Weber, Neenah, WI (US); Susan Lee West, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 394 days.

This patent is subject to a terminal disclaimer.

(21) Appl. No.: 12/692,103

(22) Filed: Jan. 22, 2010

(65) Prior Publication Data
US 2010/0121293 A1 May 13, 2010

Related U.S. Application Data

(63) Continuation of application No. 11/033,201, filed on Jan. 11, 2005, now Pat. No. 7,695,464, which is a continuation of application No. 10/676,442, filed on Sep. 30, 2003, now Pat. No. 6,847,067, which is a continuation of application No. 09/444,083, filed on Nov. 22, 1999, now Pat. No. 6,761,711.

(60) Provisional application No. 60/112,707, filed on Dec. 18, 1998.

(51) Int. Cl.
*A61F 13/15* (2006.01)

(52) U.S. Cl.
USPC ........... 604/389; 604/390; 604/396; 604/387; 604/386; 604/394; 604/385.27; 604/385.29

(58) Field of Classification Search
USPC ................ 604/389, 390, 396, 387, 386, 394, 604/385.27, 385.29
See application file for complete search history.

(56) References Cited

U.S. PATENT DOCUMENTS 2,957,512 A 10/1960 Wade et al.
3,039,466 A 6/1962 Wilson (Continued)

FOREIGN PATENT DOCUMENTS

CA 2096672 11/1997
DE 3533881 A1 4/1986

(Continued)

OTHER PUBLICATIONS

United States District Court Eastern District of Wisconsin (Green Bay) Civil Docket for case #: 1:09-cv-00916-WCG; downloaded from Pacer Feb. 8, 2011; 28 pages.

(Continued)

*Primary Examiner* — Jacqueline F. Stephens
(74) *Attorney, Agent, or Firm* — Armstrong Teasdale LLP

(57) ABSTRACT

A disposable absorbent article includes an absorbent chassis and a fastening system that together define a refastenable pant. The refastenable pant includes a pair of elastomeric front side panels extending from the waist opening to each leg opening, a pair of elastomeric back side panels extending from the waist opening to each leg opening, and a pair of refastenable seams extending from the waist opening to each leg opening and positioned between the elastomeric front and back side panels.

54 Claims, 6 Drawing Sheets

(56) References Cited

U.S. PATENT DOCUMENTS

| | | | |
|---|---|---|---|
| 3,277,547 A | 10/1966 | Billarant | |
| 3,316,139 A | 4/1967 | Alford et al. | |
| 3,319,307 A | 5/1967 | Marforio | |
| 3,577,607 A | 5/1971 | Ikoma et al. | |
| 3,694,867 A | 10/1972 | Stumpf | |
| 3,842,832 A | 10/1974 | Wideman et al. | |
| 3,842,837 A | 10/1974 | Sward | |
| 3,943,981 A | 3/1976 | De Brabander | |
| 4,022,211 A * | 5/1977 | Timmons et al. | 604/361 |
| 4,051,854 A | 10/1977 | Aaron | |
| 4,122,552 A | 10/1978 | Tedford | |
| 4,145,763 A | 3/1979 | Abrams et al. | |
| 4,201,203 A | 5/1980 | Applegate | |
| 4,205,679 A | 6/1980 | Repke et al. | |
| 4,209,563 A | 6/1980 | Sisson | |
| 4,244,368 A | 1/1981 | Caradonna | |
| 4,253,461 A | 3/1981 | Strickland et al. | |
| 4,259,957 A | 4/1981 | Sonenstein et al. | |
| 4,338,938 A | 7/1982 | Seavitt | |
| 4,402,690 A | 9/1983 | Redfern | |
| 4,418,123 A | 11/1983 | Bunnelle et al. | |
| 4,446,189 A | 5/1984 | Romanek | |
| 4,496,360 A | 1/1985 | Joffe et al. | |
| 4,516,975 A | 5/1985 | Mitchell | |
| 4,560,381 A | 12/1985 | Southwell | |
| 4,568,342 A | 2/1986 | Davis | |
| 4,581,772 A | 4/1986 | Smith | |
| 4,585,447 A | 4/1986 | Karami | |
| 4,610,680 A | 9/1986 | LaFleur | |
| 4,610,682 A | 9/1986 | Kopp | |
| 4,615,695 A * | 10/1986 | Cooper | 604/385.15 |
| 4,619,649 A | 10/1986 | Roberts | |
| 4,623,339 A | 11/1986 | Ciraldo et al. | |
| 4,650,483 A | 3/1987 | Joffe | |
| 4,655,760 A | 4/1987 | Morman et al. | |
| 4,657,802 A | 4/1987 | Morman | |
| 4,662,875 A | 5/1987 | Hirotsu et al. | |
| 4,663,220 A | 5/1987 | Wisneski et al. | |
| 4,699,622 A | 10/1987 | Toussant et al. | |
| 4,701,170 A | 10/1987 | Wilson et al. | |
| 4,701,176 A | 10/1987 | Wilson et al. | |
| 4,704,116 A | 11/1987 | Enloe | |
| 4,705,710 A | 11/1987 | Matsuda | |
| 4,714,096 A | 12/1987 | Guay | |
| 4,718,901 A | 1/1988 | Singheimer | |
| 4,720,415 A | 1/1988 | Vander Wielen et al. | |
| 4,725,473 A | 2/1988 | Van Gompel et al. | |
| 4,743,239 A | 5/1988 | Cole | |
| 4,756,709 A | 7/1988 | Stevens | |
| 4,761,318 A | 8/1988 | Ott et al. | |
| 4,770,656 A | 9/1988 | Proxmire et al. | |
| 4,771,483 A | 9/1988 | Hooreman et al. | |
| 4,789,699 A | 12/1988 | Kieffer et al. | |
| 4,834,742 A | 5/1989 | Wilson et al. | |
| 4,846,825 A | 7/1989 | Enloe et al. | |
| 4,847,134 A | 7/1989 | Fahrenkrug et al. | |
| 4,850,988 A | 7/1989 | Aledo et al. | |
| 4,850,992 A | 7/1989 | Amaral et al. | |
| 4,863,785 A | 9/1989 | Berman et al. | |
| 4,894,060 A | 1/1990 | Nestegard | |
| 4,895,569 A | 1/1990 | Wilson et al. | |
| 4,904,251 A | 2/1990 | Igaue et al. | |
| 4,923,456 A | 5/1990 | Proxmire | |
| 4,936,840 A | 6/1990 | Proxmire | |
| 4,938,757 A | 7/1990 | Van Gompel et al. | |
| 4,940,464 A | 7/1990 | Van Gompel et al. | |
| 4,963,140 A | 10/1990 | Robertson et al. | |
| 5,019,073 A | 5/1991 | Roessler et al. | |
| 5,024,672 A | 6/1991 | Widlund | |
| 5,032,122 A | 7/1991 | Noel et al. | |
| 5,046,272 A | 9/1991 | Vogt et al. | |
| 5,062,839 A | 11/1991 | Anderson | |
| 5,087,253 A | 2/1992 | Cooper | |
| 5,104,116 A | 4/1992 | Pohjola | |
| 5,114,781 A | 5/1992 | Morman | |
| 5,116,662 A | 5/1992 | Morman | |
| 5,125,246 A | 6/1992 | Shytles | |
| 5,151,092 A | 9/1992 | Buell et al. | |
| D331,969 S | 12/1992 | Hunt | |
| 5,176,670 A | 1/1993 | Roessler et al. | |
| 5,176,671 A | 1/1993 | Roessler et al. | |
| 5,185,052 A | 2/1993 | Chappell et al. | |
| 5,224,405 A | 7/1993 | Pohjola | |
| 5,226,992 A | 7/1993 | Morman | |
| 5,242,436 A | 9/1993 | Weil et al. | |
| 5,256,231 A | 10/1993 | Gorman et al. | |
| 5,269,776 A | 12/1993 | Lancaster | |
| 5,286,770 A | 2/1994 | Bastioli et al. | |
| 5,315,716 A | 5/1994 | Baum | |
| 5,318,555 A | 6/1994 | Siebers et al. | |
| 5,326,612 A | 7/1994 | Goulait | |
| 5,342,341 A | 8/1994 | Igaue et al. | |
| 5,370,634 A | 12/1994 | Ando et al. | |
| 5,380,313 A | 1/1995 | Goulait et al. | |
| 5,383,872 A | 1/1995 | Roessler et al. | |
| 5,385,775 A | 1/1995 | Wright | |
| 5,399,219 A | 3/1995 | Roessler et al. | |
| 5,401,275 A | 3/1995 | Flug et al. | |
| 5,407,439 A | 4/1995 | Goulait | |
| 5,413,654 A | 5/1995 | Igaue et al. | |
| 5,451,219 A | 9/1995 | Suzuki et al. | |
| 5,462,540 A | 10/1995 | Caldwell | |
| 5,476,702 A | 12/1995 | Datta et al. | |
| 5,496,298 A | 3/1996 | Kuepper et al. | |
| 5,503,908 A | 4/1996 | Faass | |
| 5,527,302 A | 6/1996 | Endres et al. | |
| 5,531,731 A | 7/1996 | Brusky | |
| 5,531,732 A | 7/1996 | Wood | |
| 5,542,942 A | 8/1996 | Kline et al. | |
| 5,546,608 A | 8/1996 | Russano | |
| 5,547,531 A | 8/1996 | Allen et al. | |
| 5,549,591 A | 8/1996 | Landvogt | |
| 5,554,239 A | 9/1996 | Datta et al. | |
| 5,569,233 A | 10/1996 | Goulait | |
| 5,591,155 A | 1/1997 | Nishikawa et al. | |
| 5,595,567 A | 1/1997 | King et al. | |
| D377,980 S | 2/1997 | Slingland | |
| 5,603,708 A | 2/1997 | Seth | |
| 5,605,735 A | 2/1997 | Zehner et al. | |
| 5,606,781 A | 3/1997 | Provost et al. | |
| 5,611,791 A | 3/1997 | Gorman et al. | |
| 5,615,460 A | 4/1997 | Weirich et al. | |
| 5,616,394 A | 4/1997 | Gorman et al. | |
| 5,620,432 A | 4/1997 | Goulait et al. | |
| 5,624,420 A | 4/1997 | Bridges et al. | |
| 5,624,427 A | 4/1997 | Bergman et al. | |
| 5,624,429 A | 4/1997 | Long et al. | |
| D379,226 S | 5/1997 | Kaczmarzyk et al. | |
| 5,643,397 A | 7/1997 | Gorman et al. | |
| 5,647,864 A | 7/1997 | Allen et al. | |
| H001674 H | 8/1997 | Ames et al. | |
| 5,655,843 A | 8/1997 | Conrad et al. | |
| 5,669,897 A | 9/1997 | Lavon et al. | |
| 5,669,900 A | 9/1997 | Bullwinkel et al. | |
| 5,681,302 A | 10/1997 | Melbye et al. | |
| 5,685,873 A | 11/1997 | Bruemmer | |
| 5,693,038 A | 12/1997 | Suzuki et al. | |
| 5,722,969 A | 3/1998 | Ito et al. | |
| 5,735,840 A | 4/1998 | Kline et al. | |
| 5,749,866 A | 5/1998 | Roe et al. | |
| 5,759,181 A | 6/1998 | Sayama et al. | |
| 5,766,389 A | 6/1998 | Brandon et al. | |
| 5,779,831 A | 7/1998 | Schmitz | |
| 5,782,819 A | 7/1998 | Tanzer et al. | |
| 5,785,699 A | 7/1998 | Schmitz | |
| 5,795,350 A | 8/1998 | Schmitz | |
| H001750 H | 9/1998 | Dobrin | |
| 5,814,178 A | 9/1998 | Jacobs | |
| 5,830,206 A | 11/1998 | Larsson | |
| 5,830,298 A | 11/1998 | Jackson | |
| 5,843,068 A | 12/1998 | Allen et al. | |
| 5,846,262 A * | 12/1998 | Sayama et al. | 604/391 |
| 5,851,205 A | 12/1998 | Hisada et al. | |
| 5,853,405 A | 12/1998 | Suprise | |

(56) References Cited

U.S. PATENT DOCUMENTS

| | | |
|---|---|---|
| 5,855,574 A | 1/1999 | Kling et al. |
| 5,858,012 A | 1/1999 | Yamaki et al. |
| 5,876,394 A | 3/1999 | Rosch et al. |
| 5,879,500 A | 3/1999 | Herrin et al. |
| 5,888,607 A | 3/1999 | Seth et al. |
| 5,891,122 A | 4/1999 | Coates |
| 5,891,547 A | 4/1999 | Lawless |
| 5,897,545 A * | 4/1999 | Kline et al. .................. 604/386 |
| 5,897,546 A | 4/1999 | Kido et al. |
| 5,897,547 A | 4/1999 | Schmitz |
| 5,899,895 A | 5/1999 | Robles et al. |
| 5,906,008 A | 5/1999 | Heki et al. |
| 5,911,713 A | 6/1999 | Yamada et al. |
| 5,921,977 A | 7/1999 | Schmitz |
| 5,925,027 A | 7/1999 | Schmitz |
| 5,926,926 A | 7/1999 | Kato |
| 5,928,212 A | 7/1999 | Kline et al. |
| 5,957,908 A | 9/1999 | Kline et al. |
| 5,967,665 A | 10/1999 | MacDonald et al. |
| 5,968,031 A | 10/1999 | Schmitz |
| 5,997,521 A | 12/1999 | Robles et al. |
| 5,997,981 A | 12/1999 | McCormack et al. |
| 6,004,306 A | 12/1999 | Robles et al. |
| 6,009,558 A | 1/2000 | Rosch et al. |
| 6,022,430 A | 2/2000 | Blenke et al. |
| 6,027,485 A | 2/2000 | Matsushita et al. |
| 6,030,373 A | 2/2000 | Van Gompel et al. |
| D421,802 S | 3/2000 | Van Gompel et al. |
| D422,077 S | 3/2000 | Suprise et al. |
| D422,078 S | 3/2000 | Vukos et al. |
| 6,063,466 A | 5/2000 | Tuschy et al. |
| 6,086,571 A | 7/2000 | Guevara et al. |
| 6,099,516 A | 8/2000 | Pozniak et al. |
| 6,113,717 A | 9/2000 | Vogt et al. |
| 6,115,847 A | 9/2000 | Rosch et al. |
| 6,146,738 A | 11/2000 | Tsuji et al. |
| D437,932 S | 2/2001 | Ruman et al. |
| D437,933 S | 2/2001 | Fletcher et al. |
| 6,192,521 B1 | 2/2001 | Alberts et al. |
| D438,614 S | 3/2001 | Ratliff et al. |
| D439,662 S | 3/2001 | Ratliff et al. |
| 6,210,388 B1 | 4/2001 | Widlund et al. |
| 6,213,991 B1 | 4/2001 | Kling et al. |
| 6,230,374 B1 | 5/2001 | Widlund |
| 6,264,643 B1 | 7/2001 | Toyoda |
| 6,287,287 B1 | 9/2001 | Elsberg |
| 6,302,871 B1 | 10/2001 | Nakao et al. |
| 6,328,725 B2 | 12/2001 | Fernfors |
| 6,329,016 B1 | 12/2001 | Shepard et al. |
| 6,332,250 B1 | 12/2001 | Igaue et al. |
| 6,352,528 B1 | 3/2002 | Weber et al. |
| 6,428,526 B1 | 8/2002 | Heindel et al. |
| 6,447,497 B1 | 9/2002 | Olson |
| 6,454,751 B1 | 9/2002 | Olson |
| 6,461,344 B1 | 10/2002 | Widlund et al. |
| 6,645,190 B1 | 11/2003 | Olson et al. |
| 6,764,475 B1 | 7/2004 | Olson |
| 6,960,197 B1 | 11/2005 | Gustafsson et al. |
| 2002/0095131 A1 | 7/2002 | Olson |
| 2002/0099353 A1 | 7/2002 | Olson |
| 2003/0060794 A1 | 3/2003 | Olson |
| 2004/0092903 A1 | 5/2004 | Olson et al. |

FOREIGN PATENT DOCUMENTS

| | | |
|---|---|---|
| DE | 19654052 C1 | 12/1997 |
| DE | 19727916 A1 | 6/1998 |
| EP | 0217032 B1 | 2/1992 |
| EP | 0520087 A1 | 12/1992 |
| EP | 0526868 A2 | 2/1993 |
| EP | 0528282 A2 | 2/1993 |
| EP | 0321232 B1 | 5/1993 |
| EP | 0320991 B1 | 5/1994 |
| EP | 0622063 A2 | 11/1994 |
| EP | 0476992 B1 | 7/1995 |
| EP | 0487921 B1 | 9/1995 |
| EP | 0433951 B1 | 8/1996 |
| EP | 0696911 B1 | 1/1997 |
| EP | 0756855 A1 | 2/1997 |
| EP | 0570980 B1 | 7/1997 |
| EP | 0597331 B1 | 11/1997 |
| EP | 0812584 A2 | 12/1997 |
| EP | 0215408 B2 | 5/1998 |
| EP | 0878180 A2 | 11/1998 |
| EP | 0757550 B1 | 12/1998 |
| EP | 0945110 A2 | 9/1999 |
| EP | 0641552 B1 | 12/1999 |
| EP | 0755239 B1 | 12/1999 |
| EP | 0800379 B1 | 12/1999 |
| EP | 0719534 B1 | 4/2000 |
| EP | 0721769 B1 | 5/2000 |
| EP | 0721770 B1 | 5/2000 |
| EP | 0547497 B2 | 7/2000 |
| EP | 0765148 B1 | 11/2000 |
| EP | 0951266 B1 | 3/2002 |
| EP | 0994689 B1 | 9/2002 |
| FR | 1375254 A1 | 10/1964 |
| GB | 1520740 A | 8/1978 |
| GB | 2088483 A | 6/1982 |
| GB | 2267024 A | 11/1993 |
| GB | 2303045 A | 2/1997 |
| GB | 2315402 A1 | 2/1998 |
| JP | 5-84322 U | 11/1993 |
| JP | 6-30962 A | 2/1994 |
| JP | 6-55623 U | 8/1994 |
| JP | 6-285113 A | 10/1994 |
| JP | 7-116191 A | 5/1995 |
| JP | 09-066071 A | 3/1997 |
| JP | 9-187477 A | 7/1997 |
| JP | 11099178 A | 4/1999 |
| TW | 286277 | 1/2006 |
| WO | 8907897 A1 | 9/1989 |
| WO | 9317648 A1 | 9/1993 |
| WO | 9502383 A1 | 1/1995 |
| WO | 9512376 A1 | 1/1995 |
| WO | 95-13775 A1 | 5/1995 |
| WO | 9501148 A1 | 5/1995 |
| WO | 9513775 | 5/1995 |
| WO | 9518589 A1 | 7/1995 |
| WO | 9527460 A1 | 10/1995 |
| WO | 9527461 A1 | 10/1995 |
| WO | 9527462 A1 | 10/1995 |
| WO | 9527463 A1 | 10/1995 |
| WO | 9529657 A1 | 11/1995 |
| WO | 9603950 A1 | 2/1996 |
| WO | 9619960 A1 | 7/1996 |
| WO | 9641604 A1 | 12/1996 |
| WO | 9704729 A1 | 2/1997 |
| WO | 9723180 A1 | 7/1997 |
| WO | 9736566 A1 | 10/1997 |
| WO | 9746197 | 12/1997 |
| WO | 9748359 A1 | 12/1997 |
| WO | 9818421 A1 | 5/1998 |
| WO | 9818422 A1 | 5/1998 |
| WO | 9851252 A1 | 11/1998 |
| WO | 9953881 A1 | 10/1999 |
| WO | 9965441 A1 | 12/1999 |
| WO | 0015069 A1 | 3/2000 |
| WO | 0019950 A1 | 4/2000 |
| WO | 0019951 A1 | 4/2000 |
| WO | 0020206 A1 | 4/2000 |
| WO | 0020207 A1 | 4/2000 |
| WO | 0023025 A1 | 4/2000 |
| WO | 0027236 A1 | 5/2000 |
| WO | 0027328 A1 | 5/2000 |
| WO | 0027329 A1 | 5/2000 |
| WO | 0030581 A1 | 6/2000 |
| WO | 0030584 A1 | 6/2000 |
| WO | 0035395 A2 | 6/2000 |
| WO | 0035396 A1 | 6/2000 |
| WO | 0035397 A1 | 6/2000 |
| WO | 0035398 A1 | 6/2000 |
| WO | 0035399 A1 | 6/2000 |

(56) References Cited

FOREIGN PATENT DOCUMENTS

| WO | 0037016 A1 | 6/2000 |
|----|------------|--------|
| WO | 0074621 A1 | 12/2000 |
| WO | 0188245 A2 | 11/2001 |

OTHER PUBLICATIONS

Protective Order signed by Judge William C. Griesbach on Jan. 29, 2010 for case # 1:09-cv-00916-WCG.
Amended Complaint against First Quality Baby Products LLC, First Quality Retail Services LLC filed by Kimberly-Clark Worldwide, Inc., Kimberly-Clark Global Sales LLC, entered Mar. 1, 2010 for case # 1:09-cv-00916-WCG.
Motion for Preliminary Injunction; filed by Kimberly-Clark Worldwide Inc., Kimberly-Clark Global Saels LLC, entered Mar. 1, 2010, for case # 1:09-cv-00916-WCG.
Finding of Facts, Conclusions of Law and Order Denying Motion for Preliminary Injunction, signed by Judge William C. Griesbach on Dec. 11, 2009, entered Dec. 11, 2009, for case # 1:09-cv-00916-WCG.
Answer to Counterclaim re filed by First Quality Baby Products LLC, First Quality Retail Services LLC, entered Dec. 10, 2009, for case # 1:09-cv-00916-WCG.
K-C's Answer to Counterclaim re Affirmative Defenses, and Counterclaims to First Quality's Answer and Counterclaims filed by Kimberly-Clark Global Sales LLC, Kimberly-Clark Worldwide Inc., entered Nov. 20, 2009, for case # 1:09-cv-00916-WCG.
K-C's Reply Brief in Support of Motion for Preliminary Injunction filed by Kimberly-Clark Global Sales LLC, Kimberly-Clark Worldwide Inc., entered Nov. 12, 2009, for case # 1:09-cv-00916-WCG.
Declaration of G.A.M. (Tony) Butterworth filed by Kimberly-Clark Global Sales LLC, Kimberly-Clark Worldwide Inc., entered on Nov. 12, 2009, for case # 1:09-cv-00916-WCG.
Declaration of Daniel T. Flaherty in Support of Kimberly-Clark Worldwide, Inc.'s and Kimberly-Clark Global Sales, LLC's Reply in Support of Their Motion for a Preliminary Injunction, entered Nov. 10, 2009, for case # 1:09-cv-00916-WCG.
Answer to Complaint, with Jury Demand, Counterclaim against Kimberly-Clark Global Sales LLC, Kimberly-Clark Worldwide Inc. filed by First Quality Retail Services LLC, First Quality Baby products LLC, entered Nov. 3, 2009 for case # 1:09-cv-00916-WCG.
First Quality Baby Products' LLC and First Quality Retail Services, LLC Brief in Opposition to Plaintiffs' Motion for a Preliminary Injunction, entered Nov. 3, 2009, for case # 1:09-cv-00916-WCG. (Redacted).
Declaration of John Blevins in Support of First Quality Baby Products, LLC and First Quality Retail Services LLC Opposition to Kimberly-Clark Worldwide, Inc. and Kimberly-Clark Global Sales LLC's Motion for a Preliminary Injunction, entered Nov. 3, 2009, for case # 1:09-cv-00916-WCG. (Redacted).
Declaration of Christopher P. Olson, entered Sep. 30, 2009, for case # 1:09-cv-00916-WCG.
Declaration of Robert Thibault, entered Sep. 30, 2009, for case # 1:09-cv-00916-WCG.
Brief in Support of Motion for Preliminary Injunction filed by Kimberly-Clark Global Sales LLC, Kimberly-Clark Worldwide Inc., entered Sep. 30, 2009, for case # 1:09-cv-00916-WCG.
Complaint against First Quality Baby Products LLC, First Quality Retail Services LLC filed by Kimberly-Clark Worldwide Inc., Kimberly-Clark Global Sales LLC, entered Sep. 22, 2009, for case # 1:09-cv-00916-WCG.
First Quality's Supplemental Non-Infringement and Invalidity Contentions; for case # 1:09-cv-00916-WCG, dated Aug. 13, 2010; 171 pages.
First Quality's Second Supplemental Non-Infringement and Invalidity Contentions; for case # 1:09-cv-00916-WCG, dated Sep. 16, 2010; 78 pages.
Kimberly-Clark's Memorandum in Support of Its Proposed Claim Construction; entered Nov. 19, 2010 for case # 1:09-cv-00916-WCG; 50 pages.

Kimberly-Clark's Fifth Supplement of Asserted Claims and Supporting Claim Charts for case # 1:09-cv-00916-WCG; dated Dec. 10, 2010; 9 pages.
First Quality's Responsive Claim Construction Brief; entered Dec. 17, 2010 for case # 1:09-cv-00916-WCG; 83 pages.
Minutes of the oral proceeding before the Opposition of Patent No. EP-1154745; dated Jan. 3, 2011; 22 pages.
Kimberly-Clark's Reply Memorandum in Support of Its Proposed Claim Construction; entered Jan. 7, 2011 for case # 1:09-cv-00916-WCG; 51 pages.
Claim Construction Order issued Jan. 20, 2011; for case # 1:09-cv-00916-WCG; 26 pages.
Kimberly-Clark Worldwide Inc., Statement of Facts and Arguments by the Opponent, filed with the European Patent Office on May 25, 2000, in opposition against EP 0755238 of SCA Hygiene Products AB.
Frank B. Dehn & Co., Letter to European Patent Office dated Nov. 2, 2001, regarding the opposition against EP 0755238 of SCA Hygiene Products AB.
Frank B. Dehn & Co., Letter to European Patent Office dated Nov. 23, 2001, regarding the opposition against EP 0755238 of SCA hygiene Products AB.
Board of Patent Appeals & Interferences, Ex Parte Kimberly-Clark Worldwide, Inc. (Control No. 90/006,775 Reexamination of U.S. Patent No. 6,428,526), Decision on Appeal dated Feb. 24, 2010.
Board of Patent Appeals & Interferences, Ex Parte Olson (U.S. Appl. No. 10/651,354, Decision on Appeal dated Aug. 27, 2007.
Exhibit A—Photographs of training pant sold by Kimberly-Clark Corporation under the tradename Huggies® Pull-Ups® Training Pants; 3 pages.
Exhibit B—Photographs of training pant sold by Kao Corporation in Japan under the tradename Merries Kids Torepants; 3 pages.
Exhibit C—Photographs of training pant sold by Paragon under the tradename Wal-Mart Dri-Bottoms Training Pants; 3 pages.
Exhibit D—Photographs of training pant sold by The Procter & Gamble Company under the tradename Luvs® Training Pants (unisex); 3 pages.
Exhibit E—Photographs of training pant sold by the Procter & Gamble Company in Japan under the tradename Pampers Sukusuku; 3 pages.
Exhibit F—Photographs of training pant sold by Uni-Charm Corporation in Japan under the tradename Torepan Man (Boys); 3 pages.
Exhibit G—Photographs of training pant sold by Uni-Charm Corporation in Japan under the tradename Torepan Man Step 2; 3 pages.
First Quality's Fourth Supplemental Non-Infringement and Invalidity Contentions, dated Nov. 16, 2010; 7 pages; Civil Case No. 09-C-0916.
Advertisement from One Step Ahead® catalog, Late Winter 2000, cover pages and page 26 referencing "Handy's Training Pants," and a photocopy of a package of Handy's Junior Training Pants as advertised therein.
Letter from Kenneth P. George's to the Hon. William C. Griesbach regarding *Kimberly-Clark Worldwide, Inc. et al.* v. *First Quality Baby Products, LLC et al.*, dated Jan. 14, 2011; 7 pages; Case No. 09-C-0916.
Letter from Marc S. Cooperman to the Hon. William C. Griesbach regarding *Kimberly-Clark Worldwide, Inc. et al.* v. *First Quality Baby Products et al.*, dated Jan. 18, 2011, 2 pages; Case No. 09-C-916 E.D. Wis.
Kimberly-Clark's Sixth Supplement of Asserted Claims and Supporting Claim Charts, dated Jun. 17, 2011; 10 pages; Civil Action No. 09-C-916.
First Quality's Sixth Supplemental Non-Infringement and Invalidity Contentions; dated Jun. 17, 2011; 28 pages; Case No. 09-C-0916.
First Quality's Fifth Supplemental Non-Infringement and Invalidity Contentions, dated May 6, 2010; 8 pages; Case No. 09-C-0916.
Redacted Deposition of Amy Lynn Fletcher for Civil Action No. 09-C-916 on May 24, 2011; 80 pages.
Redacted Deposition of Christopher Olson for Civil Action No. 09-C-916 on May 26, 2011; 97 pages.
Redacted Deposition of David A. Maxton for Civil Action No. 09-C-916 on May 11, 2011; 44 pages.

(56) References Cited

OTHER PUBLICATIONS

Redacted Deposition of Elizabeth E. Metz for Case No. 09-C-916 dated Mar. 11, 2010; 9 pages.
Redacted Deposition of Elizabeth Metz for Case No. 09-C-916 dated May 25, 2011; 4 pages.
Redacted Deposition of Elizabeth Metz for Case No. 09-C-916 dated Jun. 6, 2011; 10 pages.
Redacted Deposition of Kyle Kappes for Case No. 09-C-916 dated Jun. 8, 2011; 29 pages.
Deposition of Kenneth Molee for Case No. 09-C-0916 dated Oct. 3, 2011; 391 pages.
Deposition of Kenneth Molee for Case No. 09-C-0916 dated Oct. 4, 2011; 68 pages.
Redacted Deposition of Kristina Michelle Boudry for Case No. 09-C-916 dated Jul. 8, 2011; 64 pages.
Redacted Deposition of Michael G. Panian for Case No. 09-C-916 dated Jun. 23, 2011; 8 pages.
Redacted Deposition of Peter Sawin for Case No. 09-C-916 dated Jun. 17, 2011; 4 pages.
Redacted Deposition of Robert Popp for Case No. 09-C-916 dated Jun. 9, 2011; 34 pages.
Redacted Deposition of Robert Thibault—vol. 1 for Case No. 09-C-916 dated Jun. 16, 2011; 20 pages.
Redacted Deposition of Robert Thibault—vol. 2 for Case No. 09-C-916 dated Jun. 17, 2011; 4 pages.
Redacted Deposition of G.A.M. (Tony) Butterworth for Case Nos. 09-C-916 and 10-C-1118 dated Oct. 11, 2011; 12 pages.
Redacted Deposition of G.A.M. (Tony) Butterworth for Case Nos. 09-C-916 and 10-C-1118 dated Oct. 12, 2011; 47 pages.
Redacted Deposition of G.A.M. (Tony) Butterworth for Case Nos. 09-C-916 and 10-C-1118 dated Oct. 13, 2011; 58 pages.
Redacted Deposition of G.A.M. (Tony) Butterworth for Case No. 09-C-916 dated Oct. 18, 2011; 25 pages.
Exhibit 22 to Kenneth Molee's Invalidity Expert Report on the '067 patent; 17 pages.
Redacted Transcript of A. Busch dated May 17, 2011; 13 pages.
Redacted Transcript for K. Couch dated May 18, 2011; 24 pages.
Redacted Transcript of K. Herbster dated May 10, 2011; 57 pages.
Redacted Transcript of D. Murphy dated May 11, 2011; 81 pages.
Redacted Transcript of O'Connell dated May 18, 2011; 73 pages.
Redacted Transcript of O'Connell dated Jul. 8, 2011; 11 pages.
Redacted Transcript of Schlichter dated Jul. 26, 2011; 25 pages.
Decision and Order Granting First Quality's Motion for Summary Judgment of Invalidity of Claim 4 of the '751 Patent for Case No. 09-C-916 dated Sep. 12, 2012; 11 pages.
Decision and Order Granting First Quality's Motion for Summary Judgment of Invalidity of Claims 8-10 of the '067 Patent for Case No. 09-C-0916 dated Sep. 28, 2012; 26 pages.
First Quality's Third Supplemental Non-Infringement and Invalidity Contentions, dated Nov. 5, 2010; 7 pages; Case No. 09-C-0916.
K-C's First Supplemental Response to First Quality's Interrogatory No. 27, dated May 24, 2011; 6 pages; Civil Action No. 09-C-916.
K-C's Corrected Second Supplemental Response to Interrogatory No. 22, dated Jun. 17, 2011; 10 pages; Civil Action No. 09-C-916.
K-C's First Supplemental Response to First Quality's Interrogatory Nos. 23, 25, 26, 28, 29, and 35, dated Jun. 17, 2011; 8 pages; Civil Action No. 09-C-916.
K-C's Third Supplemental Response to Interrogatory No. 21, dated Jun. 17, 2011; 20 pages; Civil Action No. 09-C-916.
K-C's Third Supplemental Response to Interrogatory No. 22 and Second Supplemental Response to Interroagtory No. 29; dated Mar. 22, 2012, 7 pages; Civil Action No. 09-C-916 and Civil Action No. 10-C-1118.
Expert Report of G.A.M. (Tony) Butterworth; dated Jul. 29, 2011, 38 pages; Civil Action No. 09-C-916.
Expert Report of Kenneth J. Molee on the Invalidity of U.S. Patent No. 6,849,067, dated Jul. 29, 2011; 59 pages; Case No. 09-CV-0916 and Case No. 10-CV-1118.
Expert Report of Kenneth J. Molee on the Non-Infringement of U.S. Patent No. 6,849,067, dated Sep. 2, 2011; 19 pages; Case No. 09-CV-0916 and Case No. 10-CV-1118.
Rebuttal Expert Report of G.A.M. (Tony) Butterworth; dated Sep. 2, 2011, 60 pages; Civil Action No. 09-C-916.
First Quality's Motion for Summary Judgment that the Asserted Claims of U.S. Patent No. 6,849,067 are Invalid, dated Oct. 19, 2011; 2 pages; Civil Action No. 09-C-0916 and Civil Action No. 10-C-1118.
Memorandum in support of First Quality's Motion for Summary Judgement that the Asserted Claims of U.S. Patent No. 6,849,067 are Invalid, dated Oct. 19, 2011; 30 pages; Civil Action No. 09-CV-0916 (Consolidated with Civil Action No. 10-CV-1118).
First Quality Civil L.R. 56(b)(1)(C) Statement of Proposed Material Facts in Support of its Motion for Summary Judgement that the Asserted Claims of U.S. Patent No. 6,849,067 are Invalid; dated Oct. 19, 2011, Civil Action No. 09-CV-0916 (Consolidated with Civil Action No. 10-CV-1118); 12 pages.
Declaration of T. Wickham Schmidt in Support of First Quality's Motion for Summary Judgment that the Asserted Claims of U.S. Patent No. 6,849,067 are Invalid, dated Oct. 19, 2011; 115 pages; Civil Action No. 09-C-0916 and Civil Action No. 10-C-1118.
Declaration of Kenneth J. Molee in Support of First Quality's Motion for Summary Judgment that the Asserted Claims of U.S. Patent No. 6,849,067 are Invalid, dated Oct. 19, 2011; 2 pages; Civil Action No. 09-C-0916 (Consolidated with Civil Action No. 10-CV-1118).
K-C's Opposition to First Quality's Motion for Summary Judgment that the Asserted Claims of U.S. Patent No. 6,849,067 are Invalid; dated Dec. 21, 2011, 38 pages; Civil Action No. 09-C-0916 and Civil Action No. 10-C-1118.
K-C's (1) Responses to First Quality's Civil L.R. 56(b)(1)(C) Statement of Proposed Material Facts for the '067 Patent and (2) Statement of Additional Facts that Require the Denial of First Quality's Motion, dated Dec. 21, 2011; 27 pages; Civil Action No. 09-C-916.
Declaration of Anthony S. Baish in Support of K-C's Opposition to First Quality's Motion for Summary Judgement that the Asserted Claims of U.S. Patent No. 6,849,067 are Invalid, dated Dec. 12, 2011; 169 pages; Civil Action No. 09-CV-0916 and Civil Action No. 10-CV-1118.
First Quality's Reply in Support of Motion for Summary Judgment that the Asserted Claims of U.S. Patent No. 6,849,067 are Invalid, dated Jan. 9, 2012; 21 pages; Civil Action No. 09-C-0916 and Civil Action No. 10-C-1118.
First Quality's Reply to K-C's Statement of Additional Facts, dated Jan. 9, 2012; 21 pages; Case No. 09-C-0916 and Case No. 10-C-1118.
Declaration of T. Wickham Schmidt in Support of First Quality's Reply in Support of Motion for Summary Judgment that the Asserted Claims of U.S. Patent No. 6,849,067 are Invalid, dated Jan. 9, 2012; 152 pages; Civil Action No. 09-C-0916 and Civil Action No. 10-C-1118.
K-C's Motion for Leave to File a Sur-Reply in Opposition to First Quality's Motion for Summary Judgment that the Asserted Claims of U.S. Patent No. 6,849,067 are Invalid, dated Feb. 21, 2012; 44 pages; Civil Action No. 09-C-916 and Civil Action No. 10-C-1118.
First Quality's Combined Memorandum in Support of its Motion to Supplement the Pending Summary Judgment Record with New Evidence that all Asserted Claims of the '067 Patent are Invalid and in Opposition to K-C's Motion to File a Sur-Reply, dated Mar. 20, 2012; 10 pages; Civil Action No. 09-CV-0916 and Civil Action No. 10-CV-1118.
First Quality's Motion for Leave to Supplement the Record, dated Mar. 20, 2012; 2 pages; Civil Action No. 09-C-0916 and Civil Action No. 10-C-1118.
Declaration of Brian A. Comack in Support of First Quality's Motion to Supplement the Pending Summary Judgment Record with new Evidence that all Asserted Claims of the '067 Patent are Invalid and in Opposition to K-C's Motion to File a Sur-Reply, dated Mar. 20, 2012; 13 pages; Civil Action No. 09-C-0916 and Civil Action No. 10-C-1118.
Supplemental Declaration of Kenneth J. Molee in Support of First Quality's Motion for Summary Judgment that the Asserted Claims of

(56) References Cited

OTHER PUBLICATIONS

U.S. Patent No. 6,849,067 are Invalid, dated Mar. 20, 2012; 146 pages; Civil Action No. 09-C-0916 and Civil Action No. 10-C-1118.
K-C's Opposition to First Quality's Motion for Leave to Supplement the Pending Summary Judgment Record, dated Apr. 13, 2012; 20 pages; Civil Action No. 09-C-916 and Civil Action No. 10-C-1118.
Declaration of Katie L. Becker in Support of K-C's Opposition to First Quality's Motion for Leave to Supplement the Pending Summary Judgment Record, dated Apr. 13, 2012; 138 pages; Civil Action No. 09-C-916 and Civil Action No. 10-C-1118.
First Quality's Reply in Support of its Motion to Supplement the Pending Summary Judgment Record with New Evidence that all Asserted Claims of the '067 Patent are Invalid, dated Apr. 30, 2012; 18 pages; Civil Action No. 09-CV-0916 and Civil Action No. 10-CV-1118.
Supplemental Declaration of Brian A. Comack in Support of First Quality's Reply in Support of its Motion to Supplement the Pending Summary Judgment Record with the New Evidence that all the Asserted Claims of the '067 Patent are Invalid, dated Apr. 30, 2012; 14 pages; Civil Action No. 09-C-0916 and Civil Action No. 10-C-1118.
Order Granting Motion to Supplement and for Sur-Reply, dated May 10, 2012; 3 pages; Case No. 09-C-916.
Supplemental Memorandum in Support of First Quality's Motion for Summary Judgment that the Asserted Claims of U.S. Patent No. 6,849.067 are Invalid, dated May 24, 2012; 20 pages; Case No. 09-CV-0916 and Case No. 10-CV-1118.
First Quality's Civil L.R. 56(b)(1)(C) Statement of Proposed Material Facts in Support of its Supplemental to its Motion for Summary Judgment that the Asserted Claims of U.S. Patent No. 6,849,067 are Invalid, dated May 24, 2012; 17 pages; Case No. 09-CV-0916 and Case No. 10-CV-1118.
Declaration of Kenneth J. Molee in Support of First Quality's Supplementation to its Motion for Summary Judgment that the Asserted Claims of U.S. Patent No. 6,849,067 are Invalid, dated May 24, 2012; 172 pages; Case No. 09-C-0916 and Case No. 10-C-1118.
K-C's Opposition to First Quality's Supplementation of its Motion for Summary Judgment that the Asserted Claims of U. S. Patent No. 6,849,067 are Invalid, dated Jun. 7, 2012; 33 pages; Civil Action No. 09-C-916 and Civil Action No. 10-C-1118.
K-C's (1) Responses to First Quality's Civil L.R. 56(b)(1)(C) Statement of Proposed Material Facts in Support of its Supplementation to its Motion for Summary Judgment that the Asserted Claims of U.S. Patent No. 6,849,067 are Invalid and (2) Statement of Additional Facts that Require the Denial of First Quality's Motion, dated Jun. 7, 2012; 48 pages; Civil Action No. 09-C-916 and Civil Action No. 10-C-1118.
Declaration of G.A.M. (Tony) Butterworth in Support of K-C's Opposition to First Quality's Supplementation of its Motion for Summary Judgment that the Asserted Claims of U.S. Patent No. 6,849,067 are Invalid, dated Jun. 7, 2012; 183 pages; Civil Action No. 09-CV-0916 and Civil Action No. 10-CV-1118.
Declaration of Daniel T. Flaherty in Support of K-C's Opposition to First Quality's Supplementation of its Motion for Summary Judgment that the Asserted Claims of U.S. Patent No. 6,849,067 are Invalid, dated Jun. 7, 2012; 51 pages; Civil Action No. 09-CV-0916 and Civil Action No. 10-CV-1118.
Reply in Support of First Quality's Supplement to Motion for Summary Judgment that the Asserted Claims of U.S. Patent No. 6,849,067 are Invalid, dated Jun. 15, 2012; 20 pages; Civil Action No. 09-C-0916 and Civil Action No. 10-C-1118.
First Quality's Reply to K-C's Statement of Additional Facts, dated Jun. 15, 2012; 34 pages; Case No. 09-C-0916 and Case No. 10-C-1118.
Kimberly-Clark's Motion for Summary Judgment that First Quality's Continuous Hook Strip Training Pant Infringes Claims 8-10 of U.S. Patent No. 6,849,067, dated Nov. 21, 2011; 3 pages; Civil Action No. 09-CV-0916 and Civil Action No. 10-CV-1118.
K-C's Memorandum in Support of its Motion for Summary Judgment that First Quality's Continuous Hook Strip Training Pant Infringes Claims 8-10 of U.S. Patent No. 6,849,067, dated Nov. 21, 2011; 19 pages; Civil Action No. 09-CV-0916 and Civil Action No. 10-CV-1118.
K-C's Civil L.R. 56.2(b)(1)(C) Statement of Proposed Material Facts in Support of its Motion for Summary Judgment that First Quality's Continuous Hook Strip Training Pant Infringes Claims 8-10 of Patent No. 6,849,067, dated Nov. 21, 2011; 13 pages; Civil Action No. 09-CV-0916 and Civil Action No. 10-CV-1118.
Declaration of Daniel T. Flaherty in Support of K-C's Motion for Summary Judgment that First Quality's Continuous Hook Strip Training Pant Infringes Claims 8-10 of U.S. Patent No. 6,849,067, dated Nov. 22, 2011; 36 pages; Civil Action No. 09-C-916 (Consolidated with Civil Action No. 10-C-1118).
First Quality's Brief in Opposition to K-C's Motion for Summary Judgment that First Quality's Continuous Hook Strip training Pant Infringes Claims 8-10 of U.S. Patent No. 6,849,067, dated Jan. 13, 2012; 9 pages; Civil Action No. 09-C-0916 and Civil Action No. 10-C-1118.
First Quality's (1) Response to K-C's Civil L.R. 56.2(b)(1)(C) Statement of Proposed Material Facts in Support of its Motion for Summary Judgment that First Quality's Continuous Hook Strip Training Pant Infringes Claims 8-10 of U.S. Patent 6,849,067 and (2) Civil L R. 56(b)(2)(B)(ii) Statement of Additional Facts that require the Denial of K-C's Motion dated Jan. 13, 2012; 15 pages; Civil Action No. 09-C-0916 and Civil Action No. 10-C-1118.
Declaration of Brian A. Comack in Support of First Quality's Brief in Opposition to K-C's Motion for Summary Judgment that First Quality's Continuous Hook Strip Training Pant Infringes Claims 8-10 of U.S. Patent 6,849,067, dated Jan. 13, 2012; 8 pages; Civil Action No. 09-C-0916 and Civil Action No. 10-C-1118.
K-C's Reply in Support of its Motion for Summary Judgment that First Quality's Continuous Hook Strip Training Pant Infringes Claims 8-10 of U.S. Patent No. 6,849,067 (ECF No. 611), dated Feb. 6, 2012; 6 pages; Civil Action No. 09-C-916 and Civil Action No. 10-C-1118.
K-C's Reply to First Quality's Statement of Additional Facts Concerning K-C's Motion for Summary Judgment that First Quality's Continuous Hook Strip Training Pant Infringes Claims 8-10 of U.S. Patent No. 6,849,067 (ECF No. 611), dated Feb. 6, 2012; 6 pages; Civil Action No. 09-C-916 and Civil Action No. 10-C-1118.
Declaration of Michael L. Krashin in Support of K-C's reply in Support of it Motion for Summary Judgment that First Quality's Continuous Hook Strip Training Pant Infringes Claims 8-10 of U.S. Patent No. 6,849.067 (ECF No. 611), dated Feb. 6, 2012; 22 pages; Civil Action No. 09-C-916 and Civil Action No. 10-C-1118.

* cited by examiner

ABSORBENT ARTICLES WITH REFASTENABLE SIDE SEAMS

RELATED APPLICATIONS

This application is a continuation of application Ser. No. 11/033,201, filed Jan. 11, 2005 now U.S. Pat. No. 7,695,464, which is a continuation of application Ser. No. 10/676,442, filed Sep. 30, 2003, now U.S. Pat. No. 6,847,067, which is a continuation of application Ser. No. 09/444,083, filed Nov. 22, 1999, now U.S. Pat. No. 6,761,711, which claims the benefit of U.S. Provisional Application No. 60/112,707, filed Dec. 18, 1998.

BACKGROUND OF THE INVENTION

The present invention relates to absorbent articles which are adapted to contain body exudates. More particularly, the invention pertains to pant-like disposable absorbent articles having refastenable side seams.

Current disposable absorbent training pants for children going through the potty training stage have proved to be a particularly desirable and useful product. Such training pants generally include an absorbent chassis including a liquid impervious outer cover, a liquid pervious bodyside liner and an absorbent structure. The training pants further include elastic side panels that are permanently bonded to opposite side edges of the absorbent chassis. The chassis and side panels thereby form a unitary waist opening and two leg openings. The fit of the pants may be further enhanced by gathering means along the waist and leg openings.

The components of traditional training pants are permanently seamed together to provide a pant product. These products are particularly appealing to caregivers and are useful in the toilet training process because the pant has a very garment-like look. Children identify diaper products with babies, and most children do not like being identified with or as babies. Consequently, these children do not want to wear baby diapers, and instead prefer to wear training pants that look like adult underwear. Thus, the switch from a traditional diaper to a more garment-like or underwear-like training pant can be an important step in the toilet training process.

One drawback with current training pants, however, is that the manner of applying them is limited to being pulled on like a pant. Applying the product like a pant is advantageous in many instances, and is particularly suited for active, walking children. Even for the same child, however, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied like either a diaper or a pant permits the interior of the product to be easily checked without having to pull the product downward.

Thus, it would be desirable to have a disposable absorbent article that provides the garment-like or underwear-like look of a traditional training pant yet affords the option of being applied either like a diaper or like a pant.

SUMMARY OF THE INVENTION

In response to the above-referenced unfulfilled need in the art, a new pant-like disposable absorbent article having refastenable side seams has been discovered. The absorbent article includes a fastening system that can be repeatedly fastened, unfastened and refastened. The refastenable seams formed by the fastening system components are disposed along the sides of the absorbent article for convenience and a garment-like look similar to conventional training pants, and elastomeric side panels can be positioned on either side of the refastenable seams for fit and comfort comparable to traditional training pants.

In one embodiment, the present invention pertains to an absorbent article including an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, and a crotch region which extends between and interconnects the front and back waist regions. The front waist region defines a pair of transversely opposed front side panels and a front center panel positioned between and interconnecting the front side panels. Similarly, the back waist region defines a pair of transversely opposed back side panels and a back center panel positioned between and interconnecting the back side panels. At least one pair of side panels is elastomeric in a direction generally parallel to the transverse axis. The absorbent chassis includes a bodyside liner, an outer cover bonded to the bodyside liner, and an absorbent assembly disposed between the bodyside liner and the outer cover. The absorbent article also includes a fastening system for releasably securing the absorbent article in a pant-like configuration. The fastening system includes first and second fastening components disposed on the back side panels and adapted to releasably engage first and second mating fastening components disposed on the front side panels. Further, the transverse distance between the first and second fastening components is substantially equal to the transverse distance between the first and second mating fastening components.

The fastening components and the mating fastening components form refastenable seams for securing front and back waist regions together. The refastenable seams allow the product to be either pulled on like a pant or applied like a diaper. If the training pant becomes soiled during use, the fastening components can be disengaged from the mating fastening components to easily remove the training pant from the waist of the wearer with reduced risk of undesirably soiling the clothes or legs of the wearer. Further, the fastening components can also be easily disengaged from the mating fastening components to inspect the training pant for possible soiling. Thus, the training pant is configured to be pulled on or off over the hips of the wearer such as conventional training pants and can be readily applied or removed by disengaging the fastening components similar to conventional diapers. Moreover, the first and second fastening components can be repositioned if necessary after the training pant has been pulled on over the legs and hips of the wearer.

The design of the absorbent chassis and the fastening components provides the absorbent article with a fastening system which is resistant to accidental disengagement of the fastening components. The location of the refastenable seams at the sides of the wearer over the hips is particularly desirable because that is an area of the absorbent article that is least subject to movements of the wearer, such as articulation of the legs. The side refastenable seams have distinct advantages over front attachment designs, which are more subject to separation forces caused by bending at the waist and movements of the legs of the wearer. Furthermore, in particular embodiments, there can be elastic panels on either side of the refastenable seams to isolate the fastening components from stress and strain caused by movement of the body. In this way, the elastic panels function in a manner similar to shock absorbers to reduce stress and strain on the fastening components. Moreover, locating the refastenable seams at the sides of the wearer maintains a garment-like look to the product and is convenient for operating the fastening components. Additionally, the fastening system components can be incorporated into the absorbent article without interfering with existing outer cover graphics, which have become an important interactive toilet training feature in current training pants.

The side panels of the absorbent article each have a waist end edge parallel to the transverse axis and forming part of one of the waist edges, as well as an opposite leg end edge. In particular embodiments, each side panel is elastomeric in a direction parallel to the transverse axis from the waist end edge to the leg end edge to provide automatic fit of the product around the wearer.

In another embodiment, the present invention pertains to an absorbent article including an absorbent chassis defining a longitudinal axis, a transverse axis, front and back waist edges parallel to the transverse axis, opposite side edges extending between the front and back waist edges, a front waist region contiguous with the front waist edge, a back waist region contiguous with the back waist edge, and a crotch region which extends between and interconnects the front and back waist regions. The absorbent chassis includes a rectangular composite structure having opposite linear side edges parallel to the longitudinal axis and opposite linear end edges parallel to the transverse axis. The composite structure includes a bodyside liner, an outer cover bonded to the bodyside liner, and an absorbent assembly disposed between the bodyside liner and the outer cover. The absorbent article also includes first and second front side panels bonded to the composite structure in the front waist region and first and second back side panels bonded to the composite structure in the back waist region. A fastening system for releasably securing the absorbent article in a pant-like configuration includes first and second fastening components connected to the respective first and second back side panels and adapted to releasably engage first and second mating fastening components connected to the respective first and second front side panels. The absorbent article also includes elastomeric components transversely disposed between the fastening components and the absorbent assembly. In this embodiment, the transverse distance between the first and second fastening components is substantially equal to the transverse distance between the first and second mating fastening components.

This embodiment of the invention provides an absorbent article that is extremely compatible with high-speed manufacturing processes. The composite structure can be formed as a generally rectangular shape and the elastomeric front and back side panels joined to the composite structure with their waist end edges forming parts of the front and back waist edges of the absorbent article.

In still another embodiment, the present invention pertains to an absorbent article including an absorbent chassis and a fastening system for releasably securing the absorbent article in a pant-like configuration. The absorbent chassis includes a rectangular composite structure, with first and second elastomeric side panels bonded to the composite structure in a first waist region and first and second elastomeric side panels bonded to the composite structure in a second waist region. Support members are bonded to, and extend transversely outward from, the first and second elastomeric side panels in the second waist region. The fastening system includes first and second fastening components disposed on the support members and adapted to releasably engage first and second mating fastening components disposed on the respective first and second elastomeric side panels in the first waist region. The elastomeric side panels in the first waist region are longitudinally spaced from the elastomeric side panels in the second waist region, and the width of the elastomeric side panels in the first waist region is the same as the width of the elastomeric side panels in the second waist region. This embodiment provides an absorbent article with a side-fastening system and equal width side panels in the opposite waist regions.

In yet another embodiment, the present invention pertains to a disposable absorbent article including an absorbent chassis and a fastening system for releasably attaching a front waist region of the absorbent chassis to a back waist region of the absorbent chassis to define a refastenable pant. The refastenable pant has a waist opening and a pair of leg openings and includes: a pair of elastomeric, nonwoven front side panels extending from the waist opening to each leg opening; a pair of elastomeric, nonwoven back side panels extending from the waist opening to each leg opening; a pair of refastenable seams extending from the waist opening to each leg opening, each refastenable seam disposed between an elastomeric front side panel and an elastomeric back side panel; and a pair of elastomeric leg members which partially encircle each leg opening.

This embodiment of the invention provides a disposable absorbent article that provides fit and comfort comparable to conventional training pants, yet provides the added benefits of refastenability. The elastomeric side panels are generally positioned over portions of the hips of the wearer and provide elasticity from the waist opening to each leg opening. The absorbent article fits closely about the body of the wearer due to the combination of the elastomeric front and back side panels, and the elastomeric leg members. The refastenable seams desirably extend from the waist opening to each leg opening to securely hold the absorbent article in place on the wearer.

The refastenable seams are formed when the first and second fastening components are engaged with the first and second mating fastening components. The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20-34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension can be aligned generally parallel to the longitudinal axis of the absorbent article and the width dimension can be aligned generally parallel to the transverse axis of the absorbent article. The term "generally parallel" as used herein refers to an angle within about 35 degrees or less of the referenced axis, and more particularly within about 20 degrees or less of the referenced axis.

The fastening components can comprise any refastenable fasteners suitable for absorbent articles, although desirably comprise mechanical fastening elements rather than adhesive fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

As disclosed in copending U.S. Patent Application Ser. No. 60/112,709, filed on Dec. 18, 1998 by C. P. Olson et al. and titled "Absorbent Articles Having Differential Strength Refastenable Seam," the refastenable seam may include one or more main refastenable attachment zones and one or more enhanced refastenable attachment zones. The main and enhanced refastenable attachment zones may be constructed to provide differential levels of securement, and particularly augmented levels of securement at locations which are subject to greater levels of separation forces.

As disclosed in copending U.S. Patent Application Ser. No. 60/112,775, filed on Dec. 18, 1998 by C. P. Olson and titled "Absorbent Articles Having Hinged Fasteners," the refastenable seam may comprise individual fastening materials with narrow spacings therebetween. The narrow spacings provide a desirable hinge to improve fit and securement of the fastening components.

The disclosed absorbent articles are adapted to be worn adjacent to the body of a wearer to absorb and contain various exudates discharged from the body. The absorbent articles are desirably pre-fastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system may be used with a wide variety of absorbent products, including training pants, diapers, incontinence garments, or other garments using mechanical or adhesive fasteners.

A detailed description of the construction and design of one form of training pant can be found in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a nonsoftened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

Figure 1:
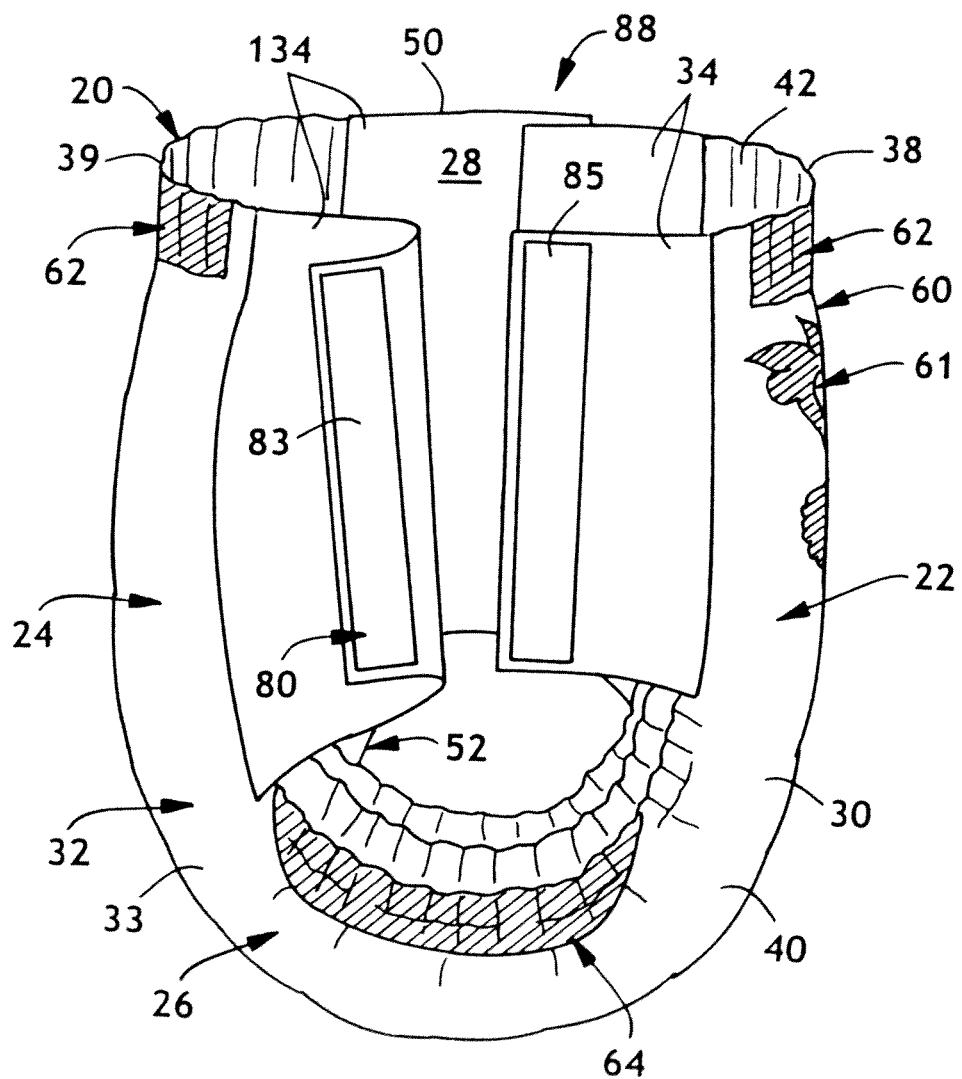
FIG. 1 illustrates a side view of one type of disposable absorbent article incorporating the principles of the present invention, where the fastening system is shown engaged on one side of the absorbent article and disengaged on the other side of the absorbent article.

With reference to FIG. 1, a disposable absorbent article, such as a training pant 20, is illustrated in a partially fastened condition. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 2:
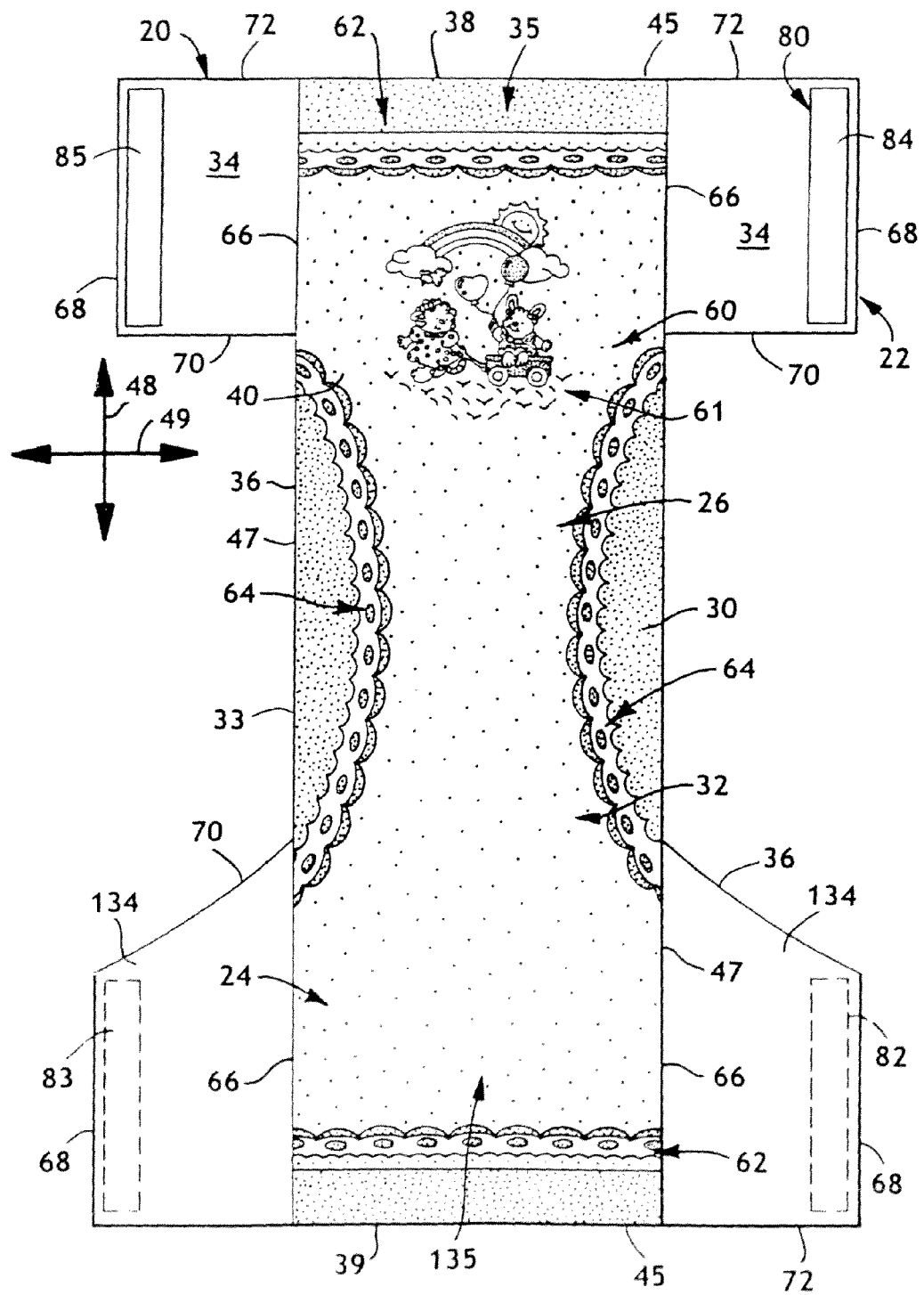
FIG. 2 illustrates a plan view of the disposable absorbent article shown in FIG. 1 in an unfastened, stretched and laid flat condition, and showing the surface of the article that faces away from the wearer.
Figure 3:
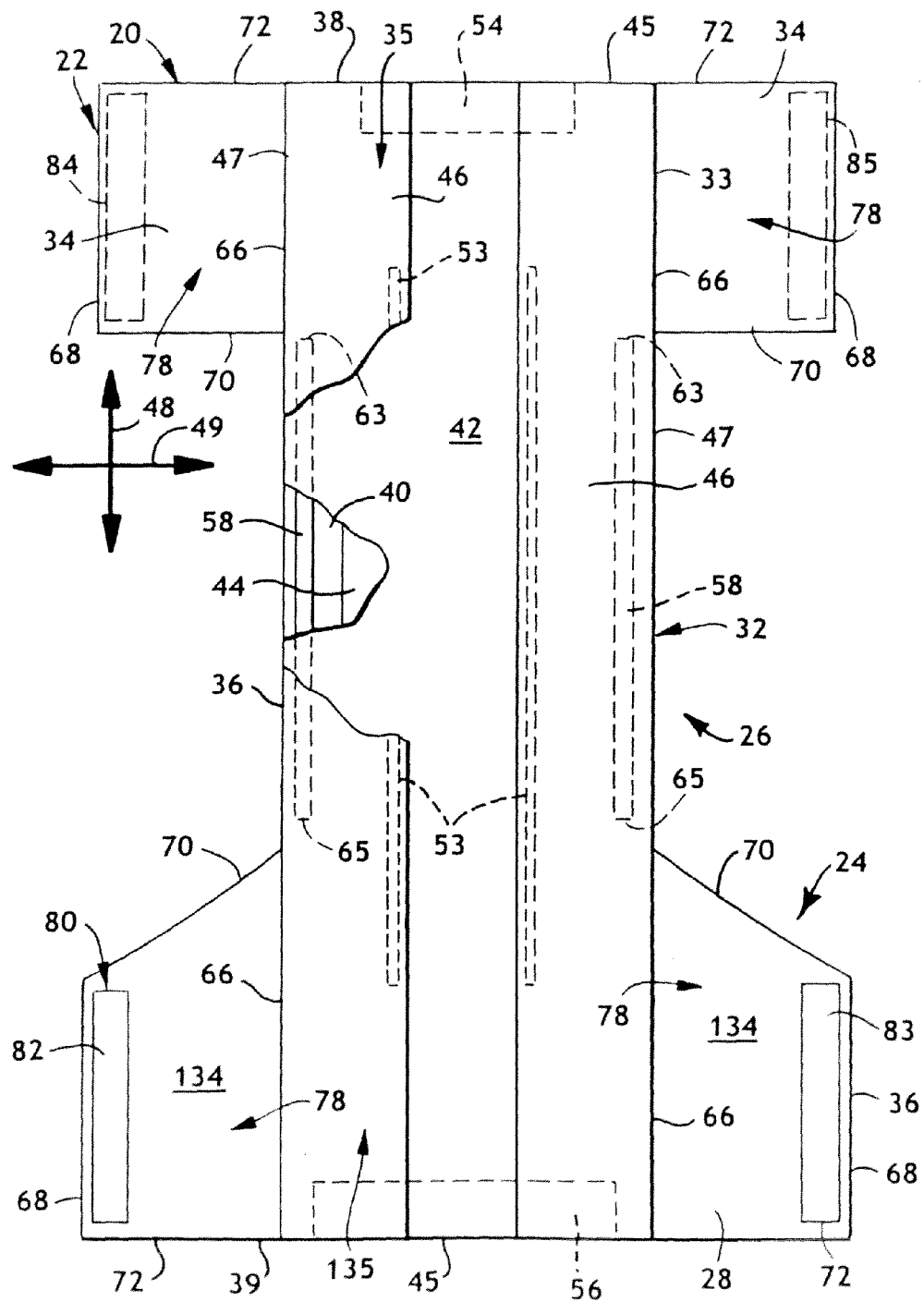
FIG. 3 illustrates a plan view similar to FIG. 2, but showing the surface of the article that faces the wearer when the article is worn, and with portions cut away to show the underlying features.

The illustrated absorbent chassis 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 2 and 3) positioned between and interconnecting the side panels. The back waist region 24 of the absorbent chassis 32 includes the transversely opposed back side panels 134 and a back center panel 135 (FIGS. 2 and 3) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 1.0 mil polyethylene film commercially available from Edison Plastics Company of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes simulated a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can comprise elastomeric materials, it can be desirable in some embodiments for the composite structure to be generally inelastic, where the outer cover, the bodyside liner and the absorbent assembly comprise materials that are generally not elastomeric.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation, in Portsmouth, Va., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back waist regions 22 and 24, and are releasably attached to one another by the fastening system 80. More particularly, as shown best in FIGS. 2 and 3, the front side panels 34 can be permanently bonded to and extend transversely beyond the linear side edges 47 of the composite structure 33 in the front waist region 22 along attachment lines 66, and the back side panels 134 can be permanently bonded to and extend transversely beyond the linear side edges of the composite structure in the back waist region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover or the bodyside liner.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions comprising an elastomeric material (see FIG. 7). Still alternatively, each individual side panel 34 and 134 can include a single piece of material which is folded over upon itself along an intermediate fold line (not shown).

The side panels 34 and 134 desirably comprise an elastic material capable of stretching in a direction generally parallel to the transverse axis 49 of the training pant 20. In particular embodiments, the front and back side panels 34 and 134 may each comprise an interior portion 78 disposed between the distal edge 68 and the respective front or back center panel 35 or 135. In the illustrated embodiment, the interior portions 78 are disposed between the distal edges 68 and the side edges 47 of the rectangular composite structure 33. The elastic material of the side panels 34 can be disposed in the interior portions 78 to render the side panels elastomeric in a direction generally parallel to the transverse axis 49. Most desirably, each side panel 34 is elastomeric from the waist end edge 72 to the leg end edge 70. More specifically, individual samples of side panel material, taken between the waist end edge 72 and the leg end edge 70 parallel to the transverse axis 49 and having a length from the attachment line 66 to the distal edge 68 and a width of 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIGS. 2 and 3). The illustrated fastening system 80 includes first and second fastening components 82 and 83 that are adapted to refastenably connect to first and second mating fastening components 84 and 85. In one embodiment, one surface of each of the first and second fastening components 82 and 83 comprises a plurality of engaging elements that project from that surface. The engaging elements of these fastening components 82 and 83 are adapted to repeatedly engage and disengage the engaging elements of the mating fastening components 84 and 85.

In one particular embodiment, the first and second fastening components 82 and 83 each comprise hook type fasteners and the first and second mating fastening components 84 and 85 each comprise complementary loop type fasteners. In another particular embodiment, the first and second fastening components 82 and 83 each comprise loop type fasteners and the first and second mating fastening components 84 and 85 each comprise complementary hook type fasteners. Although the illustrated embodiments show the back waist region 24 overlapping the front waist region 22, which is convenient, the training pant 20 can also be configured so that the front waist region overlaps the back waist region. Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 and 83 or the mating fastening components 84 and 85 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

With particular reference to FIG. 3, the first and second fastening components 82 and 83 are desirably disposed on the inner surface 28 of the training pant 20 in the back waist region 24. The first and second fastening components 82 and 83 are desirably positioned along the distal edges 68 of the back side panels 134, and abutting or adjacent to the waist end edge 72. In certain embodiments, for example, the first and second fastening components 82 and 83 are located within about 2 centimeters, and more particularly within about 1 centimeter, of the distal edges 68, the waist end edges 72, and the leg end edges 70.

With particular reference to FIG. 2, the first and second mating fastening components 84 and 85 are disposed on the outer surface 30 of the training pant 20 in the front waist region 22. The first and second mating fastening components 84 and 85 are sized to receive the first and second fastening components 82 and 83 and are desirably positioned along the distal edges 68 of the front side panels 34, and abutting or adjacent to the waist end edge 72. In certain embodiments, for example, the first and second mating fastening components 84 and 85 are located within about 2 centimeters, and more particularly within about 1 centimeter, of the distal edges 68, the waist end edges 72, and the leg end edges 70. Where the fastening components 82 and 83 comprise loop type fasteners disposed on the inner surface 28 and the mating fastening components 84 and 85 comprise hook type fasteners disposed on the outer surface 30, the fastening components can be sized larger than the mating fastening components to ensure coverage of the rigid, outwardly-directed hooks.

For the refastenable seams 88 to be located at the sides of the wearer, it is particularly desirable for the transverse distance between the first and second fastening components 82 and 83 to be substantially equal to the transverse distance between the first and second mating fastening components 84 and 85. The transverse distance between a set of fasteners is the distance measured parallel to the transverse axis 49 between the longitudinal centerlines of the fasteners, measured with the side panels 34 and 134 in an unstretched condition.

The fastening components and the mating fastening components 82-85 can be adhered to the side panels 34 and 134 by any means known to those skilled in the art such as adhesive bonds, sonic bonds or thermal bonds. In an alternative embodiment, the training pant 20 includes only a single mating fastening component disposed in the front waist region 22 for refastenably connecting the fastening components 82 and 83 (not shown). In a further alternative embodiment, the fastening components and mating fastening components can comprise integral portions of the side panels. For instance, the elastomeric front side panels 34 can function as a mating fastening component in that they can comprise a material that is releasably engageable with the fastening components 82 and 83. The first and second mating fastening components 84 and 85 are desirably rectangular, although they may alternatively be square, round, oval, curved or otherwise nonrectangularly shaped.

When the fastening components and the mating fastening components 82-85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it is desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components and the mating fastening components 82-85 form a refastenable seam 88 (FIG. 1). In particular embodiments, each of the fastening components and the mating fastening components 82-85 defines a length dimension aligned generally parallel with the longitudinal axis 48 of the training pant 20 and a width dimension aligned generally parallel with the transverse axis 49 of the training pant. For a child of about 9 to about 15 kilograms (20-30 pounds), for example, the length dimension of the fastening components and mating fastening components is desirably from about 5 to about 13 centimeters, such as about 10 centimeters, and the width dimension is desirably from about 0.5 to about 3 centimeters, such as about 1 centimeter. The fastening components and the mating fastening components desirably have a length-to-width ratio of about 2 or greater, such as about 2 to about 25, and particularly about 5 or greater, such as about 5 to about 8.

The refastenable seams 88 desirably extend substantially the entire distance between the waist opening 50 and the leg openings 52 when the fastening components 82-85 are engaged. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82-85 can be formed to cover about 80 to 100 percent, and more particularly about 90 to about 98 percent, of the distance between the waist end edge 70 and the leg end edge 72 of the side panels 34 and 134.

The absorbent chassis 32 and the fastening system 80 together define a refastenable pant having a waist opening 50 and a pair of leg openings 52. When the fastening system is engaged, it can be appreciated that the refastenable pant includes a pair of elastomeric front side panels 34 extending from the waist opening to each leg opening, a pair of elastomeric back side panels 134 extending from the waist opening to each leg opening, a pair of refastenable seams 88 extending from the waist opening to each leg opening and positioned between the elastomeric front and back side panels, an elastomeric front waistband 54 disposed in the front waist region and positioned between the pair of elastomeric front side panels, an elastomeric back waistband 56 disposed in the back waist region and positioned between the pair of elastomeric back side panels, and a pair of elastomeric leg members 58 which partially encircle each leg opening. Each elastomeric leg member 58 extends from adjacent an elastomeric front side panel 34 in the front waist region 22 to adjacent an elastomeric back side panel 134 in the back waist region 24.

Figure 4:
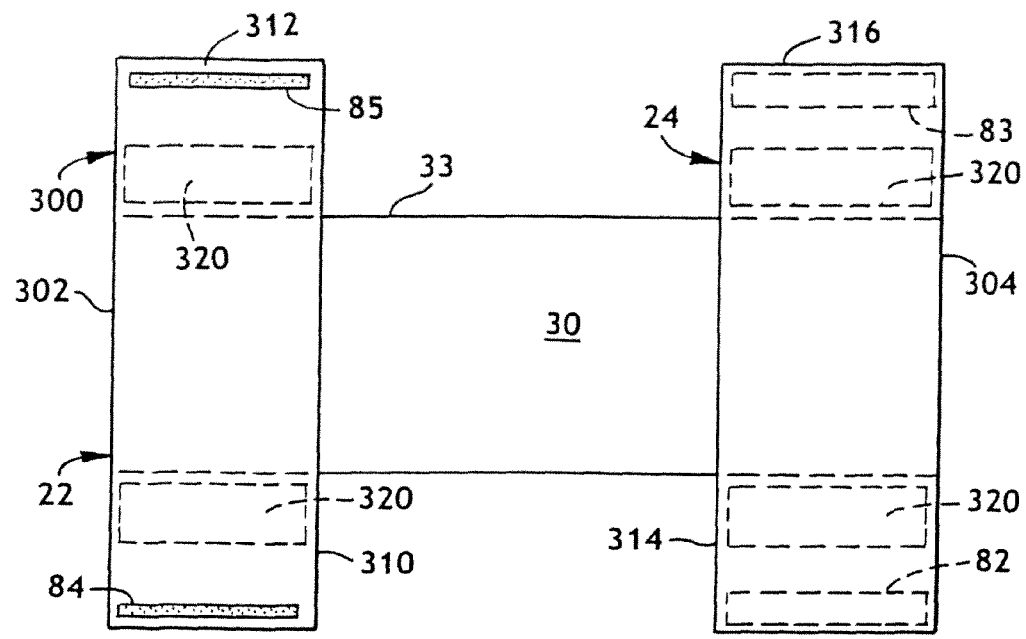
FIG. 4 illustrates a plan view of an alternative disposable absorbent article shown in an unfastened, stretched and laid flat condition, and showing the surface of the article that faces away from the wearer.

An alternative training pant 300 is illustrated in a stretched and laid flat condition in FIG. 4. The training pant 300 includes panel members 302 and 304 that are disposed respectively in the front and back waist regions 22 and 24. The panel member 302 in the front waist region 22 forms first and second side panels 310 and 312 that extend transversely outward from the composite structure 33 and the absorbent assembly 44 (FIG. 3). Similarly, the panel member 304 in the back waist region 24 forms first and second side panels 314 and 316 that extend transversely outward from the composite structure 33 and the absorbent assembly 44.

The training pant 300 also includes first and second fastening components 82 and 83 bonded to the inner surface 28 of the back attachment panels 314 and 316, and first and second mating fastening components 84 and 85 bonded to the outer surface 30 of the front attachment panels 310 and 312. In one particular embodiment, the fastening components 82 and 83 comprise loop type fasteners and the mating fastening components 84 and 85 comprise hook type fasteners that are directed outward, away from the body to minimize the chance of skin irritation.

Figure 5:
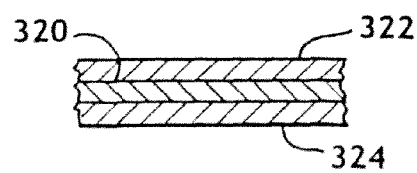
FIG. 5 illustrates an enlarged sectional view of a portion of a side panel of the absorbent article shown in FIG. 4.

The panel members 302 and 304 can each comprise an integral portion of a component of the composite structure 33, such as the bodyside liner 42 or a layer of the outer cover 40; or comprise a separate element bonded to the composite structure; or comprise a plurality of layers, whether integral portions, separate elements, or a combination thereof. Alternatively, the panel members 302 and 304 can represent portions of a single unitary member, such as a component of the composite structure 33, for example, an elastic or stretchable outer cover (not shown). The panel members 302 and 304 and thus the side panels 310, 312, 314 and 316 can comprise either elastic or inelastic materials. With additional reference to FIG. 5, the panel members 302 and 304 in the illustrated embodiment comprises a plurality of elastomeric segments 320 disposed between an outer facing layer 322 and an inner facing layer 324.

The elastomeric segments 320 can be positioned and arranged so that the side panels 310, 312, 314 and 316 have elastic properties in a direction generally parallel to the transverse axis 49 of the training pant 300. The elastomeric segments 320 can comprise elastomeric films, webs, strands, fibers or the like, and can comprise elastic materials similar to those described in relation to other elastic components of the training pants 20 and 300. The facing layers 322 and 324 can comprise materials of the type described in relation to the bodyside liner 42, the side panels 34, or the like.

Figure 6:
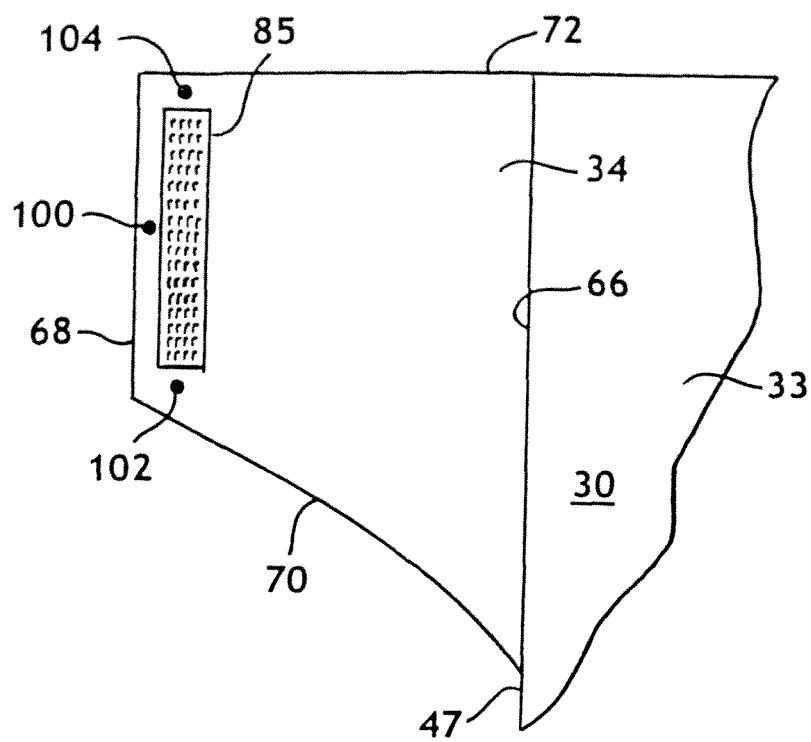
FIG. 6 illustrates an enlarged plan view of a side panel of the type shown in FIG. 1.

An enlarged plan view of a side panel 34 of the type shown in FIG. 1 is illustrated in FIG. 6. Only one side panel 34 is shown in FIG. 6, although it should be understood that other side panels can employ a similar construction. The side panel 34 can be bonded to and extend transversely beyond the linear side edge 47 of the composite structure 33 along attachment line 66. The side panel 34 defines a distal edge 68 that is spaced from the attachment line 66, a leg end edge 70 disposed toward the longitudinal center of the training pant 20, and a waist end edge 72 disposed toward a longitudinal end of the training pant.

In particular embodiments, the fastening component 85 is spaced inward from the distal edge 68 and the end edges 70 and 72 in order to protect the wearer from irritation that might be caused by contact with the fastening component. Specifically, the fastening component 85 can be spaced transversely inward from the distal edge 68 in the region of reference numeral 100. Also, the fastening component 85 can be spaced longitudinally inward from the leg end edge 70 in the region of reference numeral 102, and spaced longitudinally inward from the waist end edge 72 in the region of reference numeral 104.

The degree of spacing balances the fact that a smaller distance is harder for children and parents to remove but provides a more garment-like appearance, while a larger distance is easier for children and parents to remove but provides a loose and floppy appearance that is not garment-like. Thus, the fastening component 85 is desirably spaced transversely inward from the distal edge 68 by about 1 to about 15 millimeters, particularly about 1 to about 5 millimeters, such as about 2 millimeters. The fastening component 85 is desirably spaced longitudinally inward from the leg end edge 70 and from the waist end edge 72 by about 2 millimeters or more, particularly about 5 millimeters or more, such as from about 5 to about 15 millimeters.

Figure 7:
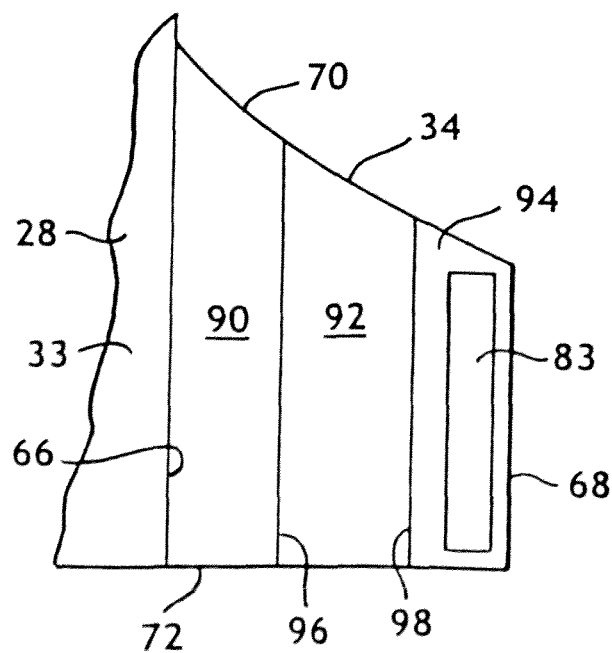
FIG. 7 illustrates an enlarged plan view of a portion of an alternative side panel.

A single side panel 34 of an alternative disposable absorbent article is shown in FIG. 7. The side panel 34 is bonded to a composite structure 33 at an attachment line 66. The side panel 34 includes a distal edge 68 transversely spaced from the attachment line 66 and a leg end edge 70 and a waist end edge 72 that extend from the composite structure to the distal edge. The side panel 34 illustrated in FIG. 7 includes a separate first member 90, second member 92, and third member 94 that are arranged in series from the attachment line 66 to the distal edge 68. The fastening component 83 is disposed on the third member 94 adjacent the distal edge 68.

The first member 90 is attached to the second member 92 at a seam 96, and the second member is attached to the third member 94 at a seam 98. The illustrated seams 96 and 98 extend from the leg end edge 70 to the waist end edge 72 of the side panel 34. The seams may be permanent seams or manually tearable seams. Suitable permanent seams can be formed by adhesives, sonic or thermal bonds, or some combination thereof, and are designed to resist tearing. Suitable manually tearable seams can be formed using means such as ultrasonic bonds to permit the side panel 34 to be torn easily at or along the seam by the caregiver. Such seams are suitably formed as lap seams or fin seams. In particular embodiments, the first and second members 90 and 92 comprise elastomeric materials and the third member 94 comprises a non-elastomeric material. Alternatively, the side panel may comprise two members, one or both of which may be elastomeric, that are bonded together at either a tearable seam or a permanent seam (not shown).

Figure 8:
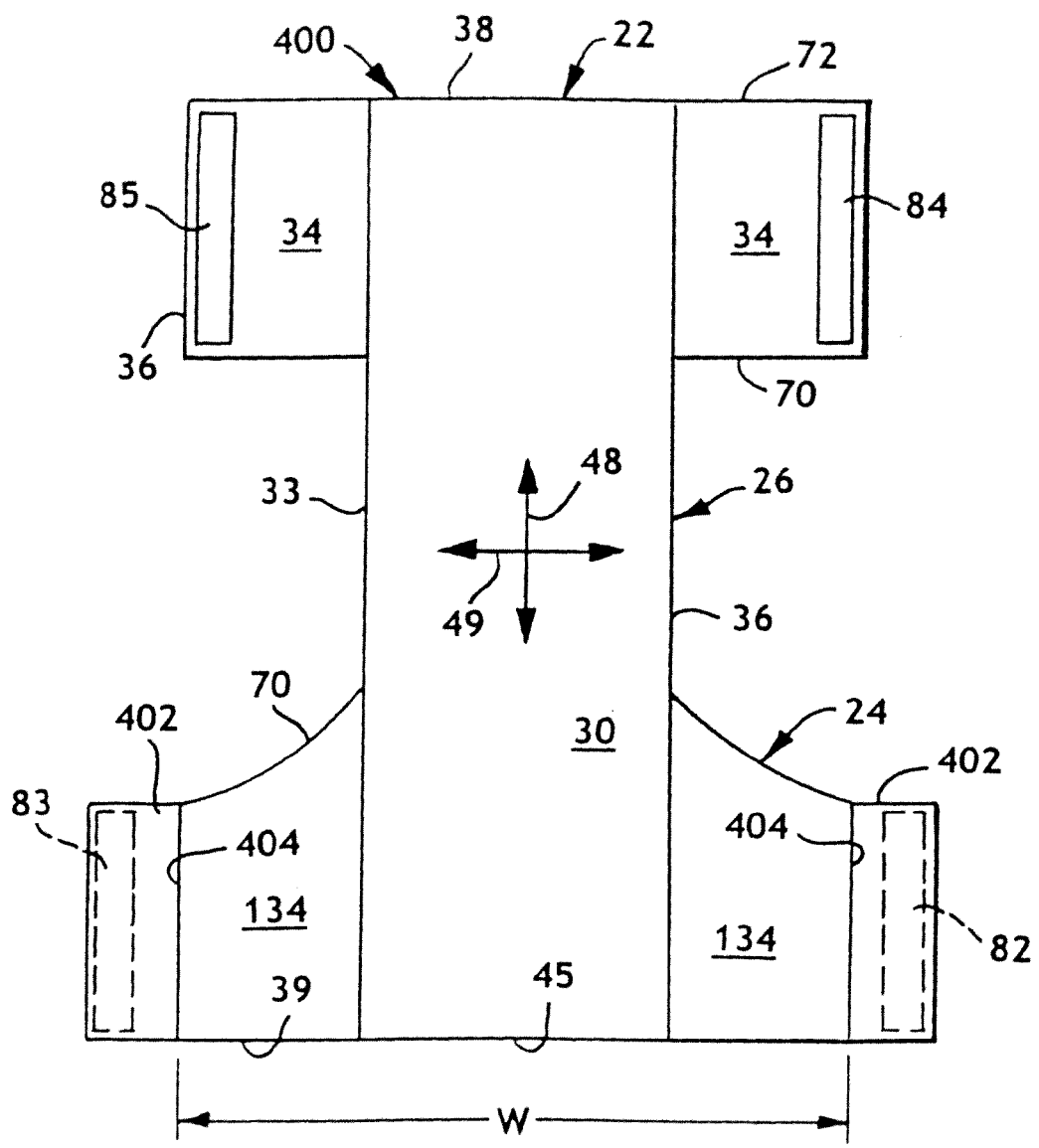
FIG. 8 illustrates a plan view of a further alternative disposable absorbent article shown in an unfastened, stretched and laid flat condition, and showing the surface of the article that faces away from the wearer.

A further alternative training pant 400 is illustrated in a stretched and laid flat condition in FIG. 8. The training pant 400 includes an absorbent chassis defining a longitudinal axis 48, a transverse axis 49, front and back waist edges 38 and 39 parallel to the transverse axis, and opposite side edges 36 extending between the front and back waist edges. The training pant 400 has a front waist region 22 contiguous with the front waist edge 38, a back waist region 24 contiguous with the back waist edge 39, and a crotch region 26 which extends between and interconnects the front and back waist regions. The illustrated absorbent chassis includes a rectangular composite structure 33, with a pair of elastomeric front side panels 34 bonded to the composite structure in the front waist region 22 and a pair of elastomeric back side panels 134 bonded to the composite structure in the back waist region 24. Desirably, the side panels 34 in the front waist region 22 are longitudinally spaced from the side panels 134 in the back waist region 24.

The illustrated training pant 400 also includes a pair of support members 402 that are bonded to and extend transversely outward from the back side panels 134. The support members 402 desirably although not necessarily comprise inelastic materials that are bonded to the side panels 134 at seams 404 using adhesives, sonic or thermal bonds, or the like. Alternatively, the training pant 400 can include support members 402 that are bonded to and extend transversely outward from both the front and back side panels 34 and 134, or from the front side panels alone (not shown).

The fastening system for the training pant 400 includes first and second fastening components 82 and 83 disposed on the support members 402. The fastening components 82 and 83 are adapted to releasably engage first and second mating fastening components 84 and 85 that are connected to the respective front side panels 34. The fastening components 82 and 83 can comprise separate structures bonded to the support members 402 or comprise integral portions, surfaces or regions of the support members. For instance, the support members 402 can comprise loop materials that function as the fastening components 82 and 83. For improved manufacturing performance, the width of the elastomeric side panels 34 in the front waist region 22 is equal to the width of the elastomeric side panels 134 in the back waist region 24. The width of the side panels 34 and 134 is represented in FIG. 8 by arrow W and excludes the width of the support members 402.

The training pants 20, 300 and 400 can further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. patent application Ser. No. 09/100,574 titled "Disposable Absorbent Articles Having Passive Side Bonds And Adjustable Fastening Systems" filed Jun. 19, 1998 by Elsberg, which is incorporated herein by reference.

As described herein, the various components of the training pants 20, 300 and 400 can be integrally assembled together employing various types of suitable attachment means, such as adhesive, sonic and thermal bonds or combinations thereof.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A training pant for use in training a child to use the toilet, comprising:
    an absorbent chassis defining a longitudinal axis, a transverse axis, an overall length dimension parallel to the longitudinal axis, front and back waist edges parallel to the transverse axis, opposite side edges extending between the front and back waist edges, a front waist region contiguous with the front waist edge, a back waist region contiguous with the back waist edge, and a crotch region which extends between and interconnects the front and back waist regions, the absorbent chassis comprising:
        a composite structure having opposite linear side edges generally parallel to the longitudinal axis and opposite linear end edges generally parallel to the transverse axis, the composite structure comprising:
        (a) a liquid permeable bodyside liner;
        (b) a liquid impermeable outer cover bonded to the bodyside liner, the outer cover comprising a liquid impermeable inner layer and a nonwoven outer layer;
        (c) an outer cover graphic disposed on the outer cover;
        (d) an absorbent assembly comprising hydrophilic fibers disposed between the bodyside liner and the outer cover; and
        (e) leg elastic members longitudinally aligned along the side edges of the composite structure;
    first and second front side panels bonded to the composite structure in the front waist region, each front side panel having a distal edge, an interior portion between the distal edge and the composite structure, a waist end edge generally parallel to the transverse axis and disposed toward a longitudinal end of the training pant, and a leg end edge extending from the respective side edge of the composite structure to the distal edge and disposed toward the longitudinal center of the training pant, the front side panels having an average length dimension that is about 20 percent or greater of the overall length dimension of the absorbent chassis;

first and second back side panels bonded to the composite structure in the back waist region and longitudinally spaced from the first and second front side panels, each back side panel having a distal edge, an interior portion between the distal edge and the composite structure, a waist end edge generally parallel to the transverse axis and disposed toward a longitudinal end of the training pant, and a leg end edge extending from the respective side edge of the composite structure to the distal edge and disposed toward the longitudinal center of the training pant, the back side panels having an average length dimension that is about 20 percent or greater of the overall length dimension of the absorbent chassis, an elastomeric material disposed between nonwoven facing layers in at least the interior portion of each back side panel to render each back side panel elastomeric in a direction generally parallel to the transverse axis; and a fastening system for releasably securing the absorbent chassis in a pant-like configuration having a waist opening and a pair of leg openings, the fastening system comprising first and second fastening components adapted to releasably engage first and second mating fastening components, the first and second fastening components being disposed on the respective first and second back side panels adjacent the distal edges, the first and second mating fastening components being disposed on the respective first and second front side panels adjacent the distal edges, the fastening components and the mating fastening components each comprising mechanical fasteners, and engagement of the fastening components and mating fastening components defines refastenable seams that cover about 80 to 100 percent of a distance between the waist opening and the leg openings.

2. The training pant of claim 1 wherein the composite structure is a rectangular composite structure.

3. The training pant of claim 1, wherein each of the first and second front side panels and the first and second back side panels has an inner surface and an opposite outer surface, and the first and second fastening components comprise loop type fasteners disposed on the outer surface of the first and second back side panels and the first and second mating fastening components comprise hook or mushroom type fasteners disposed on the inner surface of the first and second front side panels.

4. The training pant of claim 3 wherein the first and second fastening components are sized larger than the first and second mating fastening components.

5. The training pant of claim 4 wherein the loop type fasteners comprise integral portions of the back side panels.

6. The training pant of claim 3 wherein each mating fastening component is spaced inward from the distal edge, the waist end edge, and the leg end edge of the respective front side panel.

7. The training pant of claim 1 wherein the fastening components comprise integral portions of the back side panels, and wherein the mating fastening components are connected to the front side panels.

8. The training pant of claim 7 wherein the mating fastening components have a length-to-width ratio of about 5 or greater.

9. The training pant of claim 8 wherein each front side panel leg end edge is generally parallel to the transverse axis, and wherein each back side panel leg end edge is angled relative to the transverse axis.

10. The training pant of claim 1 wherein each front side panel waist end edge forms part of the front waist edge, and wherein each back side panel waist end edge forms part of the back waist edge.

11. The training pant of claim 1 further comprising a pair of containment flaps located along the entire length of the absorbent chassis along the opposite side edges of the absorbent chassis, each containment flap including at least one flap elastic member and each containment flap defining an at least partially unattached edge.

12. The training pant of claim 1 further comprising an elastomeric front waist elastic member and an elastomeric back waist elastic member.

13. The training pant of claim 1 wherein the outer cover graphic includes simulated elastic leg band components and simulated elastic waistband components, and wherein the outer cover graphic further includes registered wetness indicators.

14. The training pant of claim 1 further comprising a surge layer adapted to receive and temporarily store liquid along a mutually facing surface with the absorbent assembly.

15. The training pant of claim 1 wherein the leg elastic members have front terminal points located adjacent longitudinally innermost parts of the front side panels and back terminal points located adjacent longitudinally innermost parts of the back side panels.

16. The training pant of claim 1 wherein the training pant is prefastened to provide a pant-like product for the user.

17. The training pant of claim 1 further comprising elastomeric material disposed between nonwoven facing layers in at least the interior portion of each front side panel to render each front side panel elastomeric in a direction generally parallel to the transverse axis.

18. The training pant of claim 1 wherein the front side panels are non-stretchable.

19. The training pant of claim 1 wherein each of the first and second front side panels and the first and second back side panels has an inner surface and an opposite outer surface, and the first and second fastening components comprise hook or mushroom type fasteners connected to the outer surface of the first and second back side panels and the first and second mating fastening components comprise loop type fasteners disposed on the inner surface of the first and second front side panels.

20. The training pant of claim 19 wherein each fastening component is spaced inward from the distal edge, the waist end edge, and the leg end edge of the respective back side panel.

21. The training pant of claim 19 wherein the loop type fasteners are connected to the front side panels.

22. The training pant of claim 21 wherein the fastening components and the mating fastening components have a length-to-width ratio of about 5 or greater.

23. The training pant of claim 1 wherein the front side panels are longitudinally spaced from the back side panels by a distance equal to from about 35 to about 60 percent of the overall length dimension of the training pant.

24. The training pant of claim 1 further wherein the front side panels do not comprise elastic materials.

25. A training pant for use in training a child to use the toilet, comprising:

an absorbent chassis defining an inner surface, an opposite outer surface, a longitudinal axis, a transverse axis, an overall length dimension parallel to the longitudinal axis, front and back waist edges generally parallel to the transverse axis, opposite side edges extending between the front and back waist edges, a front waist region contiguous with the front waist edge, a back waist region contiguous with the back waist edge, and a crotch region which extends between and interconnects the front and back waist regions, the absorbent chassis comprising:

a rectangular composite structure having opposite linear side edges generally parallel to the longitudinal axis and opposite linear end edges generally parallel to the transverse axis, the composite structure comprising:

(a) a liquid permeable bodyside liner;

(b) a liquid impermeable outer cover bonded to the bodyside liner, the outer cover comprising a liquid impermeable inner layer and a nonwoven outer layer;

(c) an outer cover graphic disposed on the outer cover, wherein the outer cover graphic includes simulated elastic leg band components and simulated elastic waistband components, and wherein the outer cover graphic further includes at least one registered wetness indicator;

(d) an absorbent assembly comprising hydrophilic fibers and superabsorbent material disposed between the bodyside liner and the outer cover;

(e) a surge layer adapted to receive and temporarily store liquid along a mutually facing surface with the absorbent assembly;

(f) an elastomeric front waist elastic member and an elastomeric back waist elastic member; and (g) leg elastic members longitudinally aligned along the side edges of the composite structure;

a pair of containment flaps located along the entire length of the absorbent chassis along the opposite side edges of the absorbent chassis, each containment flap including at least one flap elastic member and each containment flap defining an at least partially unattached edge;

first and second front side panels bonded to the composite structure in the front waist region, each front side panel having a distal edge, an interior portion between the distal edge and the composite structure, a waist end edge generally parallel to the transverse axis and disposed toward a longitudinal end of the training pant, and a leg end edge extending from the respective side edge of the rectangular composite structure to the distal edge and disposed toward the longitudinal center of the training pant, each front side panel leg end edge being generally parallel to the transverse axis, each front side panel having an average length dimension that is about 20 percent or greater of the overall length dimension of the absorbent chassis;

first and second back side panels bonded to the composite structure in the back waist region and longitudinally spaced from the first and second front side panels, each back side panel having a distal edge, an interior portion between the distal edge and the composite structure, a waist end edge generally parallel to the transverse axis and disposed toward a longitudinal end of the training pant, and a leg end edge extending from the respective side edge of the rectangular composite structure to the distal edge and disposed toward the longitudinal center of the training pant, each back side panel having an average length dimension that is about 20 percent or greater of the overall length dimension of the absorbent chassis, an elastomeric material disposed between nonwoven facing layers in at least the interior portion of each back side panel to render each back side panel elastomeric in a direction generally parallel to the transverse axis; and a fastening system for releasably securing the absorbent chassis in a pant-like configuration having a waist opening and a pair of leg openings, the fastening system comprising:

first and second loop type fastening components disposed on an outer surface of and comprising integral portions of the first and second back side panels; and first and second hook or mushroom type mating fastening components disposed on an inner surface of and connected to the first and second front side panels adjacent the distal edges, each mating fastening component having a length-to-width ratio of about 5 or greater, wherein the fastening components are releasably engaged with the mating fastening components to define refastenable seams that cover about 80 to 100 percent of a distance between the waist opening and the leg openings, wherein the training pant is prefastened to provide a pant-like product for the user.

26. The training pant of claim 25, further comprising elastomeric material disposed between nonwoven facing layers in at least the interior portion of each front side panel to render each front side panel elastomeric in a direction generally parallel to the transverse axis.

27. The training pant of claim 25 wherein the front side panels are non-stretchable.

28. The training pant of claim 25 wherein the front side panels are longitudinally spaced from the back side panels by a distance equal to from about 35 to about 60 percent of the overall length dimension of the training pant.

29. The training pant of claim 25 further wherein the front side panels do not comprise elastic materials.

30. A training pant for use in training a child to use the toilet, comprising:

an absorbent chassis defining an inner surface, an opposite outer surface, a longitudinal axis, a transverse axis, an overall length dimension parallel to the longitudinal axis, front and back waist edges generally parallel to the transverse axis, opposite side edges extending between the front and back waist edges, a front waist region contiguous with the front waist edge, a back waist region contiguous with the back waist edge, and a crotch region which extends between and interconnects the front and back waist regions, the absorbent chassis comprising:

a rectangular composite structure having opposite linear side edges generally parallel to the longitudinal axis and opposite linear end edges generally parallel to the transverse axis, the composite structure comprising:

(a) a liquid permeable bodyside liner;

(b) a liquid impermeable outer cover bonded to the bodyside liner, the outer cover comprising a liquid impermeable inner layer and a nonwoven outer layer;

(c) an outer cover graphic disposed on the outer cover, wherein the outer cover graphic includes simulated elastic leg band components and simulated elastic waistband components, and wherein the outer cover graphic further includes at least one registered wetness indicator;
(d) an absorbent assembly comprising hydrophilic fibers and superabsorbent material disposed between the bodyside liner and the outer cover;
(e) a surge layer adapted to receive and temporarily store liquid along a mutually facing surface with the absorbent assembly;
(f) an elastomeric front waist elastic member and an elastomeric back waist elastic member; and
(g) leg elastic members longitudinally aligned along the side edges of the composite structure;

a pair of containment flaps located along the entire length of the absorbent chassis along the opposite side edges of the absorbent chassis, each containment flap including at least one flap elastic member and each containment flap defining an at least partially unattached edge;

first and second front side panels bonded to the composite structure in the front waist region, each front side panel having a distal edge, an interior portion between the distal edge and the composite structure, a waist end edge generally parallel to the transverse axis and disposed toward a longitudinal end of the training pant, and a leg end edge extending from the respective side edge of the rectangular composite structure to the distal edge and disposed toward the longitudinal center of the training pant, each front side panel leg end edge being generally parallel to the transverse axis, each front side panel having an average length dimension that is about 20 percent or greater of the overall length dimension of the absorbent chassis;

first and second back side panels bonded to the composite structure in the back waist region and longitudinally spaced from the first and second front side panels, each back side panel having a distal edge, an interior portion between the distal edge and the composite structure, a waist end edge generally parallel to the transverse axis and disposed toward a longitudinal end of the training pant, and a leg end edge extending from the respective side edge of the rectangular composite structure to the distal edge and disposed toward the longitudinal center of the training pant, each back side panel having an average length dimension that is about 20 percent or greater of the overall length dimension of the absorbent chassis, an elastomeric material disposed between nonwoven facing layers in at least the interior portion of each back side panel to render each back side panel elastomeric in a direction generally parallel to the transverse axis; and a fastening system for releasably securing the absorbent chassis in a pant-like configuration having a waist opening and a pair of leg openings, the fastening system comprising:
first and second loop type fastening components connected to an inner surface of the first and second front side panels; and
first and second hook or mushroom type mating fastening components connected to an outer surface of the first and second back side panels adjacent the distal edges,
wherein the fastening components are releasably engaged with the mating fastening components to define refastenable seams that cover about 80 to 100 percent of a distance between the waist opening and the leg openings,
wherein the training pant is prefastened to provide a pant-like product for the user.

31. The training pant of claim 30 wherein the front side panels are non-stretchable.

32. The training pant of claim 30, wherein each mating fastening component has a length-to-width ratio of about 5 or greater.

33. A training pant for use in training a child to use the toilet, comprising:
an absorbent chassis defining a longitudinal axis, a transverse axis, an overall length dimension generally parallel to the longitudinal axis, front and back waist edges generally parallel to the transverse axis, opposite side edges extending between the front and back waist edges, a front waist region contiguous with the front waist edge, a back waist region contiguous with the back waist edge, and a crotch region which extends between and interconnects the front and back waist regions, the absorbent chassis comprising:
a composite structure having opposite linear side edges generally parallel to the longitudinal axis and opposite linear end edges generally parallel to the transverse axis, the composite structure comprising:
(a) a liquid permeable bodyside liner;
(b) a liquid impermeable outer cover bonded to the bodyside liner, the outer cover comprising a liquid impermeable inner layer and a nonwoven outer layer;
(c) an outer cover graphic disposed on the outer cover;
(d) an absorbent assembly comprising hydrophilic fibers disposed between the bodyside liner and the outer cover; and
(e) leg elastic members longitudinally aligned along the side edges of the composite structure;

first and second front side panels bonded to the composite structure in the front waist region, each front side panel having a distal edge, an interior portion between the distal edge and the composite structure, a waist end edge generally parallel to the transverse axis and disposed toward a longitudinal end of the training pant, and a leg end edge extending from the respective side edge of the composite structure to the distal edge and disposed toward the longitudinal center of the training pant, the front side panels having an average length dimension that is about 20 percent or greater of the overall length dimension of the absorbent chassis, an elastomeric material disposed between nonwoven facing layers in at least the interior portion of each front side panel to render each front side panel elastomeric in a direction generally parallel to the transverse axis;

first and second back side panels bonded to the composite structure in the back waist region and longitudinally spaced from the first and second front side panels, each back side panel having a distal edge, an interior portion between the distal edge and the composite structure, a waist end edge generally parallel to the transverse axis and disposed toward a longitudinal end of the training pant, and a leg end edge extending from the respective side edge of the composite structure to the distal edge and disposed toward the longitudinal center of the training pant, the back side panels having an average length dimension that is about 20 percent or greater of the overall length dimension of the absorbent chassis; and a fastening system for releasably securing the absorbent chassis in a pant-like configuration having a waist opening and a pair of leg openings, the fastening system comprising first and second fastening components adapted to releasably engage first and second mating fastening components, the first and second fastening components being disposed on the respective first and second back side panels adjacent the distal edges, the first and second mating fastening components being disposed on the respective first and second front side panels adjacent the distal edges, the fastening components and the mating fastening components each comprising mechanical fasteners, and engagement of the fastening components and mating fastening components defines refastenable seams that cover about 80 to 100 percent of a distance between the waist opening and the leg openings.

34. The training pant of claim 33 wherein the composite structure is a rectangular composite structure.

35. The training pant of claim 33 wherein each of the first and second front side panels and the first and second back side panels has an inner surface and an opposite outer surface, and the first and second fastening components comprise loop type fasteners disposed on the outer surface of the first and second back side panels and the first and second mating fastening components comprise hook or mushroom type fasteners disposed on the inner surface of the first and second front side panels.

36. The training pant of claim 35 wherein the first and second fastening components are sized larger than the first and second mating fastening components.

37. The training pant of claim 36 wherein the loop type fasteners comprise integral portions of the back side panels.

38. The training pant of claim 35 wherein each mating fastening component is spaced inward from the distal edge, the waist end edge, and the leg end edge of the respective front side panel.

39. The training pant of claim 33 wherein the fastening components comprise integral portions of the back side panels, and wherein the mating fastening components are connected to the front side panels.

40. The training pant of claim 39 wherein the mating fastening components have a length-to-width ratio of about 5 or greater.

41. The training pant of claim 40 wherein each front side panel leg end edge is generally parallel to the transverse axis, and wherein each back side panel leg end edge is angled relative to the transverse axis.

42. The training pant of claim 33 wherein each front side panel waist end edge forms part of the front waist edge, and wherein each back side panel waist end edge forms part of the back waist edge.

43. The training pant of claim 33 further comprising a pair of containment flaps located along the entire length of the absorbent chassis along the opposite side edges of the absorbent chassis, each containment flap including at least one flap elastic member and each containment flap defining an at least partially unattached edge.

44. The training pant of claim 33 further comprising an elastomeric front waist elastic member and an elastomeric back waist elastic member.

45. The training pant of claim 33 wherein the outer cover graphic includes simulated elastic leg band components and simulated elastic waistband components, and wherein the outer cover graphic further includes registered wetness indicators.

46. The training pant of claim 33 further comprising a surge layer adapted to receive and temporarily store liquid along a mutually facing surface with the absorbent assembly.

47. The training pant of claim 33 wherein the leg elastic members have front terminal points located adjacent longitudinally innermost parts of the front side panels and back terminal points located adjacent longitudinally innermost parts of the back side panels.

48. The training pant of claim 33 wherein the training pant is prefastened to provide a pant-like product for the user.

49. The training pant of claim 33 further comprising elastomeric material disposed between nonwoven facing layers in at least the interior portion of each back side panel to render each back side panel elastomeric in a direction generally parallel to the transverse axis.

50. The training pant of claim 33 wherein the back side panels are non-stretchable.

51. The training pant of claim 33 wherein each of the first and second front side panels and the first and second back side panels has an inner surface and an opposite outer surface, and the first and second fastening components comprise hook or mushroom type fasteners connected to the outer surface of the first and second back side panels and the first and second mating fastening components comprise loop type fasteners disposed on the inner surface of the first and second front side panels.

52. The training pant of claim 51 wherein the loop type fasteners are connected to the inner surface.

53. The training pant of claim 33 wherein the front side panels are longitudinally spaced from the back side panels by a distance equal to from about 35 to about 60 percent of the overall length dimension of the training pant.

54. The training pant of claim 33 further wherein the back side panels do not comprise elastic materials.

* * * * *